(12) United States Patent
Shertukde et al.

(10) Patent No.: US 7,291,111 B2
(45) Date of Patent: Nov. 6, 2007

(54) APPARATUS AND METHOD FOR NON-INVASIVE DIAGNOSING OF CORONARY ARTERY DISEASE

(75) Inventors: Hemchandra Shertukde, Simsbury, CT (US); Rekha Shertukde, Simsbury, CT (US); Peter V. Beckmann, Hartford, CT (US); Raymond McLaughlin, Hartford, CT (US)

(73) Assignee: MedScanSonics, Inc., Vernon, CT (US)

( * ) Notice: Subject to any disclaimer, the term of this patent is extended or adjusted under 35 U.S.C. 154(b) by 173 days.

(21) Appl. No.: 10/830,719

(22) Filed: Apr. 23, 2004

(65) Prior Publication Data

US 2005/0038360 A1    Feb. 17, 2005

Related U.S. Application Data

(60) Provisional application No. 60/464,777, filed on Apr. 23, 2003.

(51) Int. Cl.
*A61B 5/02* (2006.01)
*A61B 5/04* (2006.01)

(52) U.S. Cl. ............ 600/483; 600/500; 600/528; 600/509; 600/521; 600/481

(58) Field of Classification Search ......... 600/481, 600/485, 500–504, 528, 509, 521, 483
See application file for complete search history.

(56) References Cited

U.S. PATENT DOCUMENTS

| 4,362,164 | A |  | 12/1982 | Little et al. |
| 4,721,114 | A |  | 1/1988 | DuFault |
| 4,751,931 | A |  | 6/1988 | Briller |
| 4,793,361 | A |  | 12/1988 | DuFault |
| 4,881,549 | A | * | 11/1989 | Rhyne .................. 600/443 |
| 4,905,706 | A |  | 3/1990 | Duff et al. |
| 4,967,760 | A |  | 11/1990 | Bennett, Jr. et al. |
| 5,036,857 | A |  | 8/1991 | Semmlow et al. |
| 5,218,969 | A |  | 6/1993 | Bredesen et al. |
| 5,262,958 | A |  | 11/1993 | Chui |

(Continued)

FOREIGN PATENT DOCUMENTS

| EP | 1495721 A2 | 1/2005 |
| WO | WO 2005/099562 | 10/2005 |

OTHER PUBLICATIONS

Akay, M., Wavelet Applications in Medicine, IEEE Spectrum, May 1997, pp. 50-56, vol. 34, issue 5, pp. 50-56.

(Continued)

*Primary Examiner*—Navin Natnithithadha
(74) *Attorney, Agent, or Firm*—Knobbe, Martens, Olson & Bear, LLP

(57) ABSTRACT

A non-invasive diagnostic tool and method for detecting an obstruction in a coronary artery, the diagnostic tool including a signal processor adapted to receive signals corresponding to a heart beat from a plurality of acoustic sensors attached to the chest of a patient. The signal processor is programmed to identify a diastolic portion of the signals for a plurality of heartbeats and conduct a wavelet transform analysis on the diastolic signals for determining the existence of, as well as the severity and the location of, an obstruction in a coronary artery of the patient.

32 Claims, 18 Drawing Sheets

U.S. PATENT DOCUMENTS

| | | | |
|---|---|---|---|
| 5,301,679 A | 4/1994 | Taylor | |
| 5,327,893 A * | 7/1994 | Savic | 600/454 |
| 5,337,752 A | 8/1994 | Reeves | |
| 5,360,005 A | 11/1994 | Wilk | |
| 5,439,483 A | 8/1995 | Duong-Van | |
| 5,554,177 A | 9/1996 | Kieval et al. | |
| 5,590,650 A | 1/1997 | Genova | |
| 5,609,158 A | 3/1997 | Chan | |
| 5,617,869 A | 4/1997 | Austin et al. | |
| 5,638,823 A * | 6/1997 | Akay et al. | 600/528 |
| 5,687,738 A | 11/1997 | Shapiro et al. | |
| 5,749,364 A * | 5/1998 | Sliwa et al. | 600/438 |
| 5,778,881 A | 7/1998 | Sun et al. | |
| 5,957,866 A | 9/1999 | Shapiro et al. | |
| 6,048,319 A | 4/2000 | Hudgins et al. | |
| 6,050,950 A | 4/2000 | Mohler | |
| 6,053,872 A | 4/2000 | Mohler | |
| 6,178,386 B1 | 1/2001 | Shertukde et al. | |
| 6,179,783 B1 | 1/2001 | Mohler | |
| 6,193,668 B1 | 2/2001 | Chassaing et al. | |
| 6,243,599 B1 | 6/2001 | Van Horn | |
| 6,245,025 B1 | 6/2001 | Torok et al. | |
| 6,278,890 B1 | 8/2001 | Chassaing et al. | |
| 6,328,698 B1 | 12/2001 | Matsumoto | |
| 6,340,347 B1 | 1/2002 | Toda | |
| 6,368,283 B1 | 4/2002 | Xu et al. | |
| 6,371,924 B1 | 4/2002 | Stearns | |
| 6,383,143 B1 | 5/2002 | Rost | |
| 6,393,316 B1 | 5/2002 | Gillberg et al. | |
| 6,440,082 B1 | 8/2002 | Joo et al. | |
| 6,478,746 B2 | 11/2002 | Chassaing et al. | |
| 6,514,211 B1 * | 2/2003 | Baura | 600/490 |
| 6,551,256 B1 | 4/2003 | Stasz et al. | |
| 6,572,560 B1 * | 6/2003 | Watrous et al. | 600/528 |
| 6,629,937 B2 * | 10/2003 | Watrous | 600/586 |
| 6,643,548 B1 | 11/2003 | Mai et al. | |
| 6,699,201 B2 | 3/2004 | Stearns | |
| 6,898,459 B2 * | 5/2005 | Hayek et al. | 600/509 |
| 6,939,308 B2 | 9/2005 | Chassaing et al. | |
| 6,953,436 B2 * | 10/2005 | Watrous et al. | 600/528 |
| 2003/0208116 A1 * | 11/2003 | Liang et al. | 600/407 |
| 2005/0033190 A1 | 2/2005 | Bauer | |

OTHER PUBLICATIONS

Shertukde, H., Hand-held device for non-invasive coronary artery diagnostics (NICAD), 2002, sabbatical report.

Whipple, S., City Firm Develops Heart Monitoring Device, newspaper article, Jun. 28, 2002, The New Britain Herald.

Akay Y.M. et al, Noninvasive Detection of Coronary Artery Disease, IEEE Engineering in Medicine and Biology Magazine, Nov. 1, 1994, pp. 761-764, vol. 13, No. 5.

Akay M. et al, "Automated Noninvasive detection of coronary artery disease using wavelet-based neural networks," Proceedings of the 16th Annual International Conference of the IEEE Engineering in Medicine and Biology Society (Engineerig Advances: New Opportunities for Biomedical Engineers (Cat. No. 94CH3474-4), Baltimore, MD, USA Nov. 3-6, 1994, pp. 12a-13a vol. 1, XP002116721, 1994, New York, NY, USA, IEEE, USA, ISBN: 0-7803-2050-6).

Leung, T.S. et al, Acoustic diagnosis of heart diseases. In: Proceedings of the 3rd International Conference on Acoustical and Vibratory Surveillance Methods and Diagnostic Techniques, 1998, pp. 389-398, France.

Shertukde, R.H. et al., Manufacture of Fault Diagnostic Device for Electrical Power Transformers, (Proceedings ICSPAT 96, Oct. 7-10, 1996, Boston, Massachusetts, USA).

Shertukde H.M. et al., Fault Detection Device for Electrical Power Transformers Using Novel DSP Scheme, (Proceedings: International Conference on Signal Processing Applications and Technology, Boston, Massachusetts, Oct. 5-10).

Unser, M. et al., A Review of Wavelets in Biomedical Applications, Proceedings of the IEEE, vol. 84, No. 4, Apr. 1996.

Akay, M., Diagnosis of Coronary Artery Disease Using Wavelet-Based Neural Networks, Wavelets in Medicine and Biology, 1996, pp. 513-524, CRC Press, Boca Raton.

Plaintiff MedScanSonics, Inc's. Complaint in *MedScanSonics, Inc. v. Hemchandra M. Shertukde*, et al., Connecticut Superior Court, dated Apr. 28, 2006.

Plaintiff ICU Medical, Inc's. Complaint in *ICU Medical, Inc. v. Hemchandra M. Shertukde*, et al., Connecticut Superior Court, dated Apr. 28, 2006.

Correspondence between J. Bruce Boisture and Hemchandra and Rekha Shertukde.

International Search Report and Written Opinion of the International Searching Authority for International Application No. PCT/US04/12556, mailing date Mar. 7, 2005.

International Preliminary Report on Patentability for International Application No. PCT/US2004/012556, mailing date Nov. 10, 2005.

International Search Report and Written Opinion of the International Searching Authority for International Application No. PCT/US2006/002132, mailing date Jun. 23, 2006.

M. Akay et al., *Autoregressive Modeling of Diastolic Heart Sounds*, IEEE Engineering in Medicine & Biology Society 10th Annual Conference CH2566-8/88/0000-0172, 1988.

M. Akay et al., *Detection of Coronary Occlusion Using Autoregressive Modeling of Diastolic Heart Sounds*, IEEE Transaction on Biomedical Engineering 0018-9294/90/0366, Apr. 1990, vol. 37, No. 4.

M. Akay et al., *Investigation the Effects of Vasodilator Drugs on the Turbulent Sound Caused by Femoral Artery Stenosis Using Short-Term Fourier and Wavelet Transform Methods*, IEEE Transactions on Biomedical Engineering 0018-9294/94, Oct. 1994, pp. 921-928, vol. 41, No. 10.

M. Akay et al., *Noninvasive Detection of Coronary Artery Disease Using Neural Networks*, Annual International Conference of the IEEE Engineering in Medicine and Biology Society, 1991, pp. 1434-1435, vol. 13, No. 3.

Y. Akay et al., *A Comparative Study of Advanced Signal Processing Techniques for Detection of Coronary Artery Disease*, Annual International Conference of the IEEE Engineering in Medicine and Biology Society CH3068-4/91/0000-2139, 1991, pp. 2139-2140, vol. 13, No. 5.

Y. Akay et al., *Noninvasive Acoustical Detection of Coronary Artery Disease: A Comparative Study of Signal Processing Methods*, IEEE Transactions on Biomedical Engineering 0018-9294/93, Jun. 1993, pp. 571-578, vol. 40, No. 6.

Y. Akay et al., *Noninvasive Detection of Severity of Occlusions Associated with Coronary Artery Disease*, Annual International Conference of the IEEE Engineering in Medicine and Biology Society CH3068-4/91/0000-2101, 1991, pp. 2101-2102, vol. 13, No. 5.

Y. Akay et al., *Spectral Analysis of the Turbulent Sounds Caused By Femoral Artery Stenosis in Dogs*, IEEE 0-7803-9202-2/92, 1992, pp. 127-128.

Brookes, *The Definition and Consequences of Hypertension Are Evolving*, Medscape Cardiology http://www.medscape.com/viewarticle/506463, 2005.

Cohen et al, *Wavelets: The Mathematical Background*, Proceedings of the IEEE 0018-9219/96, Apr. 1996, pp. 514-522, vol. 84, No. 4.

Debiais et al., *Time-Frequency Analysis of Heart Murmurs. Part II: Optimisation of Time-Frequency Representations and Performance Evaluation*, Journal of the International Federation for Medical & Biological Engineering & Computing, Sep. 1997, pp. 480-485, vol. 35, No. 5.

Fischer et al., *Comparative Evaluation of Cardiac Microphones*, IEEE Engineering in Medicine & Biology Society 10th Annual Conference CH2566-8/88/0000-0167, 1988.

Lees et al., *Phonoangiography: A New Noninvasive Diagnostic Method for Studying Arterial Disease*, Proceedings of the National Academy of Sciences, Oct. 1970, pp. 935-942, vol. 67, No. 2.

Leung et al., *Classification of Heart Sounds Using Time-Frequency Method and Artificial Neural Networks*, Proceedings of the 22nd Annual EMBS International Conference 0-7803-6465-1/00, Jul. 2000, pp. 988-991, Chicago, U.S.A.

Li et al., *Detection of ECG Characteristic Points Using Wavelet Transforms*, IEEE Transactions on Biomedical Engineering, Jan. 1995, pp. 21-28, vol. 42, No. 1.

Liang et al., *A Heart Sound Feature Extraction Algorithm Based On Wavelet Decomposition and Reconstruction*, Proceedings of the 20th Annual International Conference of the IEEE Engineering in Medicine and Biology Society 0-7803-5164-9/98, 1998, pp. 1539-1542, vol. 20, No. 3.

Liang et al., *A Heart Sound Segmentation Algorithm Using Wavelet Decomposition and Reconstruction*, Proceeding—19th International Conference—IEEE/EMBS 0-7803-4262-3/97, Oct. 30-Nov. 2, 1997, pp. 1630-1633, Chicago, U.S.A.

Mellen et al., *Closed-Form Solution for Determining Emitter Location Using Time Difference of Arrival Measurements*, IEEE Transactions On Aerospace and Electronic Systems 0018-9251/03, Jul. 2003, pp. 1056-1058, vol. 39, No. 3.

Mittal et al., *Application of Large-Eddy Simulation to the Study of Pulsatile Flow in a Modeled Arterial Stenosis*, Journal of Biomechanical Engineering, Aug. 2001, pp. 325-332, vol. 123.

Padmanabhan et al., *Accelerometer Type Cardiac Transducer for Detection of Low-Level Heart Sounds*, IEEE Transaction on Biomedical Engineering 0018-9294/93, Jan. 1993, pp. 21-28, vol. 40, No. 1.

Padmanabhan et al., *A Dedicated System for Acoustic Detection of Coronary Artery Disease* (ADCAD), IEEE 0-7803-0785-2/92, 1992, pp. 457-458.

Pouladian et al., *Noninvasive Detection of Coronary Artery Disease by Arterio-Oscillo-Graphy*, IEEE Transaction on Biomedical Engineering 0018-9294, Apr. 2005, pp. 743-747, vol. 52, No. 4.

Reinking, *Cardiovascular Physiology*, Biology 455 Manuscript, Millersville University, Spring 2002. Millersville, U.S.A.

Semmlow et al., *Noninvasive Detection of Coronary Artery Disease Using Parametric Spectral Analysis Methods*, IEEE Engineering in Medicine and Biology 0739-5175/90/0300-0033, Mar. 1990, pp. 33-36.

Shen et al., *Automated Identification of Artifact-free Diastolic Heart Sounds*, Annual International Conference of the IEEE Engineering in Medicine and Biology Society, 1990, pp. 0569-0570, vol. 12, No. 2.

Shertukde, *Efficient Wide-Band Cross-Correlation Tracking Using Wavelet Transforms*, Proceedings ICSPAT 94, Oct. 1994, pp. 1-3, Dallas, U.S.A.

Shertukde et al., *Fault Detection Device for Electrical Power Transformers Using Novel DSP Scheme*, Oct. 1996. pp. 1219-1223.

Shertukde, *Improvement in Performance of Nuclear Pulse Processors Using Wavelet Transforms*, Proceedings ICSPAT 94, Oct. 1994, pp. 1-3, Dallas, U.S.A.

Shertukde et al., *Real Time Transformer Fault Diagnostics using Supersonic Sensors and Wavelet Transforms*, Proceedings ICSPAT 97, Sep. 1997, pp. 1341-1345, San Diego, U.S.A.

Shertukde et al., *Target Parameter Estimation in the Near Field with Two Sensors*, IEEE Transaction on Acoustics 0096-3518/88/0800-1357, Speech, and Signal Processing, Aug. 1998, pp. 1357-1360, vol. 36, No. 8.

Plett, et al., *Automated Ultrasonic Arterial Vibrometry: Detection and Measurement, Medical Imaging 2000: Ultrasonic Imaging and Signal Processing*, Proceedings of SPIE, Apr. 2000, pp. 370-378, vol. 3982.

Sierra et al., *Multiresolution Decomposition of the Signal-Averaged ECG Using the Mallat Approach for Prediction of Arrhythmic Events After Myocardial Infarction*, Journal of Electrocardiology 0018-9294/95, 1996, pp. 223-234, vol. 29, No. 3.

Wei et al., *Noninvasive Quantification of Coronary Blood Flow Reserve in Humans Using Myocardial Contrast Echocardiography*, American Heart Association, Circulation, 2001; 103:2560, http://circ.ahajournals.org/cqi/content/full/103/21/2560.

Yang et al., *Modeling and Decomposition of HRV Signals with Wavelet Transforms*, IEEE Engineering in Medicine and Biology 0739/5175/97, Jul./Aug. 1997, pp. 17-22.

Ye et al., *Noninvasive Detection Of Coronary Artery Disease Based On Heart Sounds*, Proceedings of the 20th Annual International Conference of the IEEE Engineering in Medicine and Biology Society 0-7803-5164-9/98, 1998, pp. 1546-1548, vol. 20, No. 3.

Yoshida et al., *Instantaneous Frequency Analysis of Systolic Murmur for Phonocardiogram*, Proceedings—19th International Conference—IEEE/EMBS 0-7803-4262-3/97, Oct. 30-Nov. 2, 1997, pp. 1645-1647, Chicago, U.S.A.

Suzuki et al., *The Absolute Sensitivity Characteristics of Lung-Sound Transducers Coupled to Chest Wall*, Proceedings of the 20th Annual International Conference of the IEEE Engineering in Medicine and Biology Society, 0-7803-5164-9/98, 1998, pp. 1727-1730, vol. 20, No. 4.

Young, *Wavelet Theory and its Applications*, Kluwer Academic Publishers 0-7923-9271-X, 1993, Norwell, U.S.A.

Peter V. Beckmann, Hardware Development of a Coronary Artery Disease Detection Device Using Signal Characteristics Analysis, dated May 2003, Masters Thesis for the College of Engineering, University of Hartford, Hartford, Connecticut.

Raymond W. McLaughlin, Systems Considerations and Software for Non-Invasive Diagnostics of Coronary Artery Disease, dated May 2003, Masters Thesis for the College of Engineering, University of Hartford, Hartford, Connecticut.

Correspondence between J. Bruce Boisture and Hemchandra and Rekha Shertukde, Sep. 13, 2006.

\* cited by examiner

APPARATUS AND METHOD FOR NON-INVASIVE DIAGNOSING OF CORONARY ARTERY DISEASE

CROSS REFERENCE TO RELATED APPLICATIONS

This application claims priority to U.S. Provisional Patent Application No. 60/464,777 filed on Apr. 23, 2003 entitled "Coronary Artery Diagnostics Using Signal Characteristic Analysis (CADSCAN)". The disclosure of the above-identified provisional application is incorporated herein by reference.

FIELD OF THE INVENTION

The present invention generally relates to coronary artery disease and more particularly to an apparatus and method for determining the severity and location of a stenosis in a coronary artery of a patient using non-invasive signal processing techniques.

BACKGROUND OF THE INVENTION

Coronary artery disease generally refers to a build-up of cholesterol or plaque on the interior walls of the arteries of the heart. FIG. 1 is an illustration of an artery 10 having a layer of plaque 12 formed on the interior walls of the artery. This type of build-up of plaque 12 reduces the capacity of the affected arteries to carry blood thereby reducing the flow of blood through the arteries and the amount of blood delivered to the muscles the arteries supply. The plaque 12 can also weaken the walls of affected arteries. As shown in FIG. 2, a crack 14 may develop in the plaque 12 and cause a blood clot to form in an artery. Many heart attacks are caused by blood clots in the coronary arteries.

Currently, angiograms are widely used to diagnose coronary artery disease. An angiogram is an invasive procedure that usually requires cardiac catheterization wherein a catheter is inserted into the blood vessel being examined. FIG. 3 shows a prior art catheter 16 shown inserted into a patient's 18 blood vessel 20 starting near the patient's groin and extending through the blood vessel and into the patient's heart 22. This type of catheterization process is normally necessary before angiogram and subsequent angioplasty procedures are conducted. Normally, attached to the end of the catheter are suitable sensors. In some cases, the sensors are active sensor heads, which emit a radio frequency signal of about 1 MHz and project it towards the heart. These sensor heads are often positioned close to a patient's heart. The projected signal is reflected off the arteries of the heart and can be used to determine an approximate location of an occlusion. An angioplasty is done by inserting a cleaning tool through the artery to remove an occlusion. In some cases, both the angiogram and the angioplasty processes are agonizing for the patient and can be dangerous or even fatal.

When an obstruction occurs in an artery, the blood flow through the affected artery creates more turbulence than in an unobstructed artery. This turbulence normally generates high frequency sounds especially during the diastolic activity of the heart. High frequency bandwidth, spread spectrum signals that experience time and frequency scaling are difficult to decompose with narrow band analysis, such as Fourier transform, due to its sinusoidal kernel, which approximates the scaling effect with a Doppler shift. However, this type of high frequency signal represents an admissible kernel representation for using wavelet transform (WT) in appropriate signal processing algorithms. A wavelet transform analysis uses a more general analysis kernel, or mother wavelet.

In "Wavelet Applications in Medicine" by Akay et. al, IEEE Spectrum, 1997 pages 50-56, there are described techniques used in signal processing for detection of coronary artery disease in healthy and unhealthy patients. Although such technology has been proposed as providing a reliable measurement, the technology has not been fully developed and the multiplicity of acoustic sensors proposed has represented a substantial impediment to widespread usage.

Based on the foregoing, it is the general object of the present invention to provide an apparatus and method for diagnosing coronary artery disease that improves upon, or overcomes the problems and drawbacks associated with prior art methods and tools for diagnosing coronary artery disease.

Another object of the present invention is to provide a novel apparatus for detecting and determining the position of obstructions in a patient's coronary arteries.

A further object of the present invention is to provide a novel method of detecting the location of and the severity of obstructions in the coronary arteries.

It is also an object of the present invention to provide such an apparatus, which can be readily available, and that is reliable and relatively inexpensive.

Another object of the present invention is to provide an apparatus for detecting and determining the position of obstructions in a patient's coronary arteries, which may be constructed from readily available components at a reasonable cost to enable the widespread use thereof.

A still further object of the present invention is to provide a non-invasive method of determining the location and the severity of obstructions in the coronary arteries.

REFERENCES

[1] Metin Akay; "Wavelet Applications in Medicine", IEEE Spectrum, vol. 34, issue 5, pp50-56, May 1997.
[2] Hemchandra Shertukde, "Hand-held device for non-invasive coronary artery diagnostics (NICAD)", sabbatical report, 2002.

SUMMARY OF THE INVENTION

The present invention is directed to a non-invasive diagnostic tool for detecting an obstruction in a coronary artery. The diagnostic tool includes a signal processor adapted to receive signals corresponding to a heart beat from a plurality of acoustic sensors attached to the chest of a patient. The signal processor is programmed to identify a diastolic portion of the signals for a plurality of heartbeats and to analyze the diastolic portion of the signals to determine the location of an obstruction in a coronary artery and the severity thereof. The diagnostic tool includes a display coupled to the signal processor for displaying data indicative of the results of the diagnosis. A user interface is coupled to the signal processor for providing user control of the diagnostic tool. In one embodiment, the diagnostic tool of the present invention is a portable hand-held device that is attachable to a plurality of acoustic sensors.

The diagnostic tool includes an analog to digital converter coupled to the signal processor and is adapted to receive signals from the acoustic sensors and process the signals including at least one of digitizing, synchronizing and multiplexing the signals, and to transmit the processed signals to the signal processor. The signal processor is programmed to conduct a wavelet transform on the signals. The wavelet transform provides time domain and frequency analysis on the signals for determining the location and severity of an occlusion in a patient's coronary arteries.

The present invention also provides a method for detecting an obstruction in a coronary artery of a patient having a plurality of acoustic sensors attached to his/her chest. The method receiving a signal from each of a plurality of acoustic sensors attached to the chest of a patient at known locations. The signals represent a plurality of heart beats of the patient. A threshold amplitude frequency range is established for identifying the signals to be evaluated. The signals are processed for determining the existence of, as well as the severity of an obstruction in a coronary artery. The method further includes a step of determining a location of the obstruction relative to the location of one of the acoustic sensors.

The step of processing includes amplifying, digitizing, synchronizing and multiplexing the signals for further processing. The processing further includes identifying a diastolic portion of the signals and the existence of a triggering pulse in the diastolic portion exceeding an established threshold amplitude that is within a predetermined frequency range. A triggering pulse vibration that exceeds the threshold amplitude indicates the existence of an occlusion in one of the coronary arteries.

The processing step further includes conducting a wavelet transform analysis on various combinations of the signals received from the acoustic sensors. The wavelet transform analysis provides time delay and frequency analysis of the signals for calculating translational delay parameters and scale parameters between any two of the signals. The translational delay parameters and the scale parameters are used to estimate the time delays for the triggering pulse heart sounds detected at the sensors. The time delays are then evaluated to determine the location of the occlusion in one of the coronary arteries. A value of the translation and scale parameters where the sum of the wavelet coefficient function is a maximum is identified and used to determine the severity of the occlusion.

BRIEF DESCRIPTION OF THE DRAWINGS

The foregoing and still other objects and advantages of the present invention will be more apparent from the detailed explanation of the preferred embodiments of the invention in connection with the accompanying drawings wherein throughout the figures, like reference numerals describe like elements of the invention.

DESCRIPTION OF THE PREFERRED EMBODIMENTS

Figure 1:
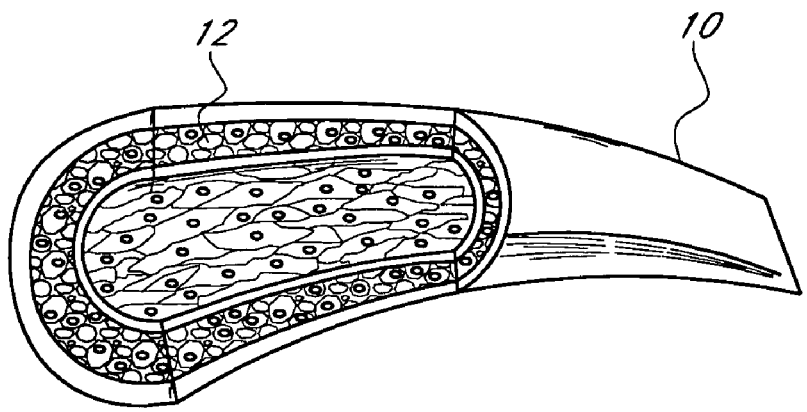
FIG. 1 is an illustration of a coronary artery showing a build-up of plaque on the inside wall thereof.
Figure 2:
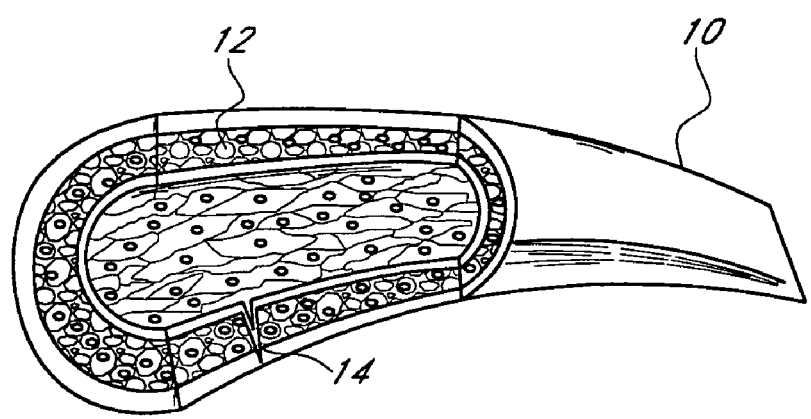
FIG. 2 is an illustration of the coronary artery of FIG. 1 including a crack defined by the plaque.
Figure 3:
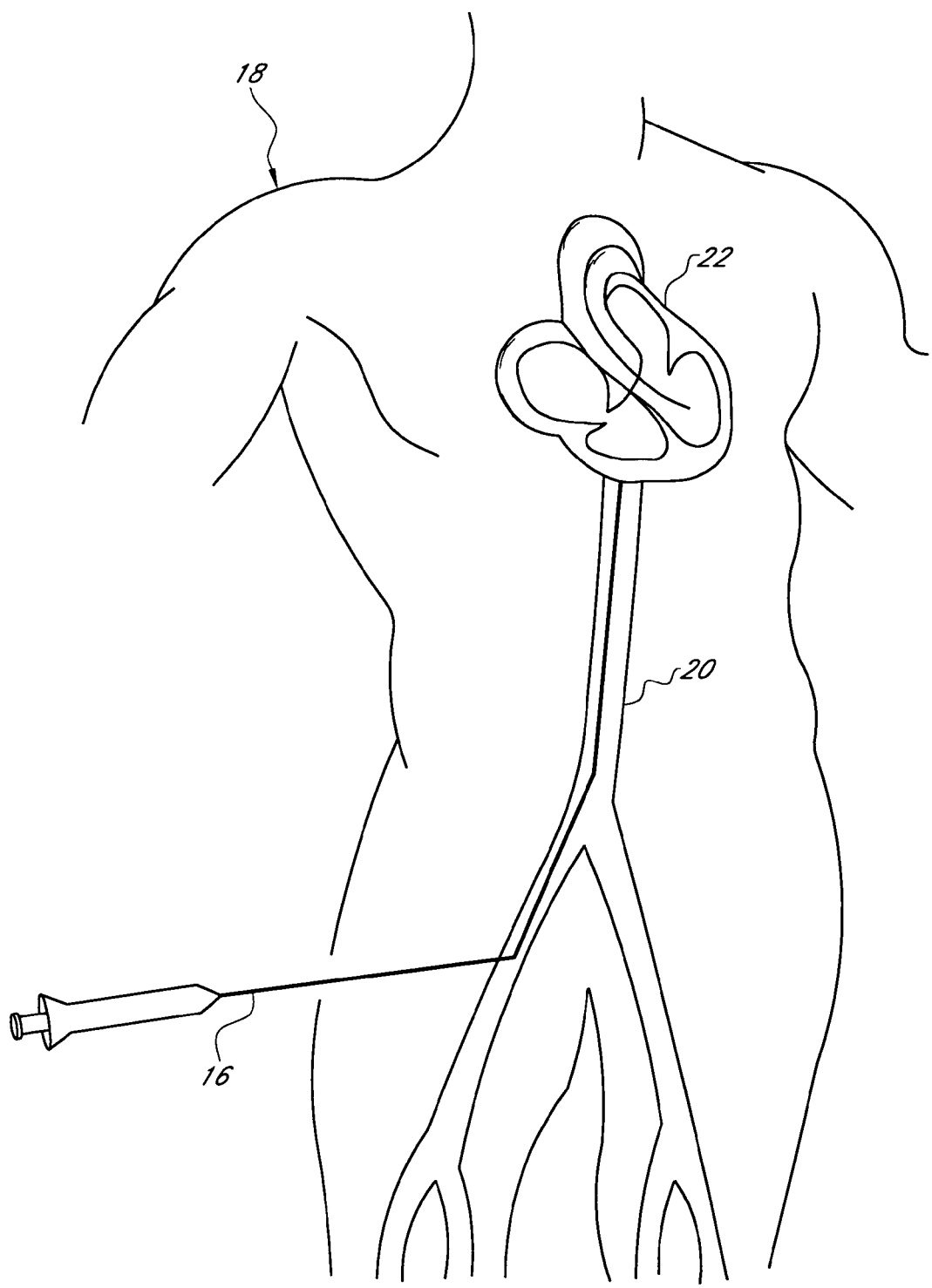
FIG. 3 shows a prior art catheter device as used during an angiogram procedure on a patient.
Figure 4:
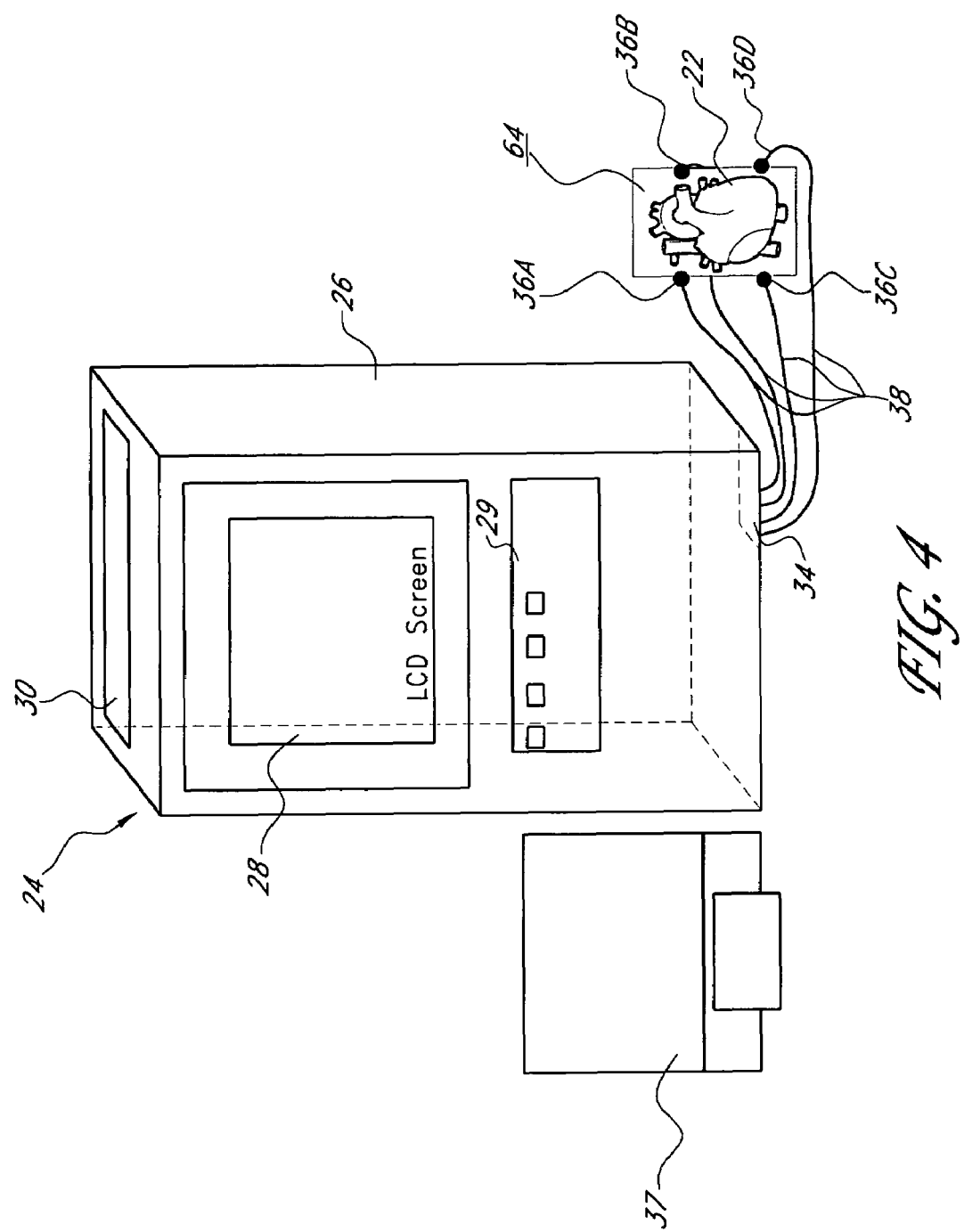
FIG. 4 is a perspective view of one embodiment of a diagnostic tool according to the present invention shown coupled to a plurality of sensors attached to the chest of a patient.
Figure 5:
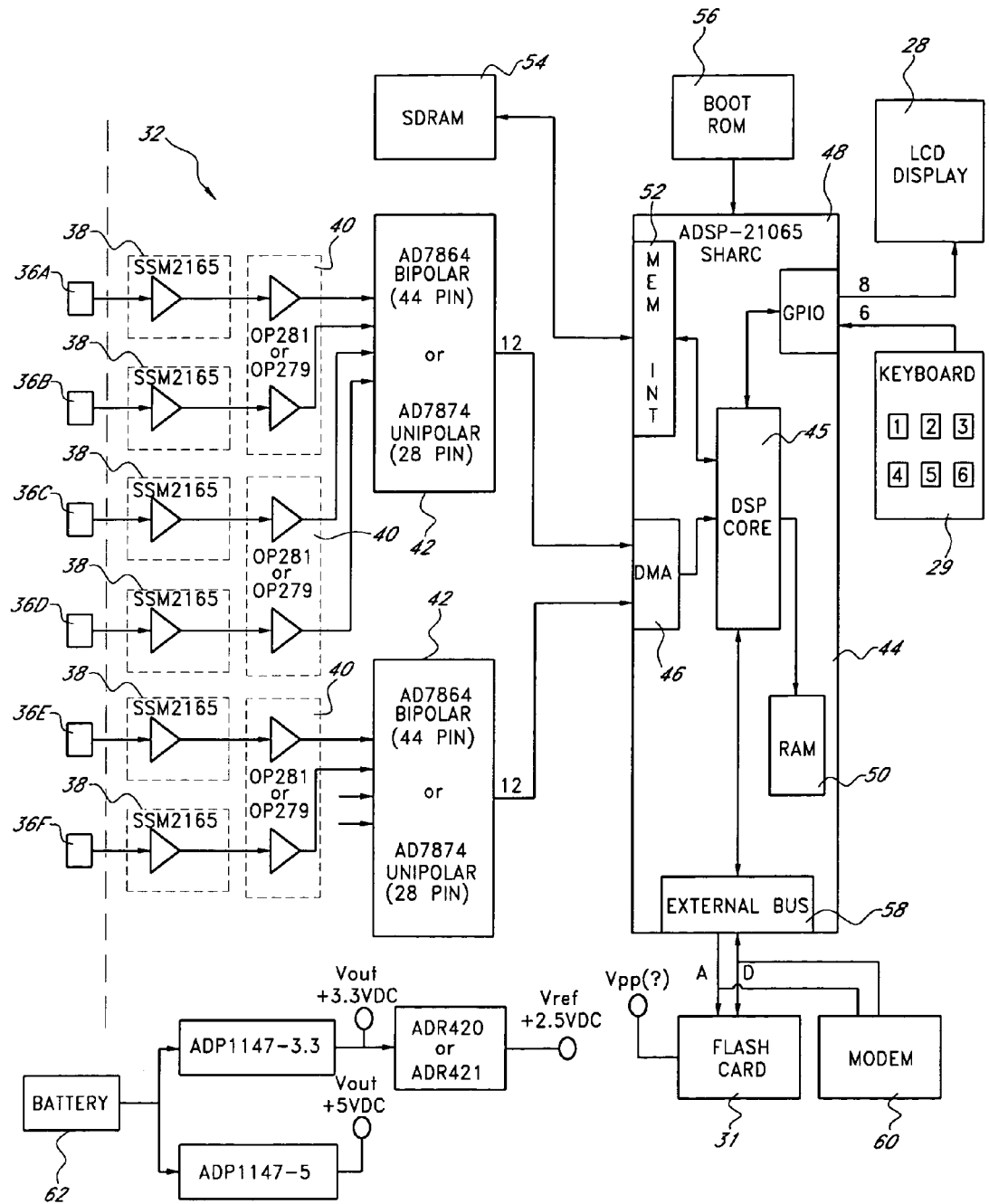
FIG. 5 is a schematic diagram of the hardware of one embodiment of the diagnostic tool of the present invention.

As shown in FIGS. 4 and 5, the present invention is directed to a diagnostic tool for detecting an obstruction in a coronary artery. In the illustrated embodiment, the diagnostic tool is a portable hand-held unit generally designated by the reference number 24. The diagnostic tool 24 includes a housing 26 supporting a display 28 and a keyboard 29. A slot 30 is defined by the housing 26 for receiving a flash memory card or flash card 31. In one embodiment, the housing 26 can be generally rectangular and can have dimensions three inches in width, five inches in height, and 0.75 inches in depth. The display 28 can be an LCD screen and it can be 1.75 inches square.

The diagnostic tool 24 includes a processor unit, generallly indicated by the reference numeral 32, disposed inside the housing 26. An interface 34 couples a plurality of acoustic sensors 36A-36F via cables 38 to the processing unit 32. In the illustrated embodiment the sensors 36A-36F are ultrasonic patches adhered to the chest of a patient 18 for monitoring the heart beats of the patient and transmitting signals indicative of the heart sounds, as will be discussed further hereinbelow. A typical sensor 37 is shown in FIG. 4.

A pre-amplifier 38 is coupled to each of the sensors 36A-36F for amplifying the signal received from the sensors and transmitting the amplified signals to a plurality of operational amplifiers 40 coupled thereto. In the illustrated embodiment, the operational amplifiers 40 are single ended low noise amplifiers having a frequency response that is flat to 1 kHz with a nominal gain of approximately 18 decibels. The operational amplifiers include outputs coupled to at least one analog to digital converter 42. The analog to digital converters 42 are for at least one of digitizing, multiplexing, synchronizing and localizing of the signals received from the operational amplifiers 40 and for transmitting the digital signals to a digital signal processor unit 44 via a dynamic memory access 46. As shown in FIG. 5 by way of example, the analog to digital converters 42 are Analog Devices® AD 7864.

The digital signal processor unit 44 includes a digital signal processor core, (DSP core) 45 coupled to the analog to digital converters 42 for processing the signals received from the sensors 36A-36F. The DSP core 45 is coupled to the display 28 and keyboard 29 via a general purpose input/output interface 48. The processing unit 44 also includes random access memory (RAM) 50 coupled to the DSP core 45 as well as an SDRAM interface 52 for coupling the DSP core to SDRAM memory 54. A Read Only Memory (ROM)

56 is coupled to the DSP core 45 for storing start-up or boot instructions for the DSP core. An external bus 58 is coupled to the DSP core 45 for coupling the flash card 31 to the DSP core as well as a modem 60. Both of the flash card 31 and the modem 60 are provided for transferring data between the DSP core and external devices. The diagnostic tool 24 also includes a battery 62 mounted in the housing 26 for supplying electrical power to the processor unit 32.

The illustrated embodiment of the present invention includes a portable hand-held diagnostic tool 24; however, the present invention is not limited in this regard. In other embodiments, a diagnostic tool in accordance with the present invention can be arranged as a self-standing tool or mountable in a housing that supports other related diagnostic tools.

The digital signal processor unit 44 is programmed with and includes software designed to process and analyze the signals generated by the sensors 36A-36F for determining a location and severity of an obstruction in one or more of the patient's 18 coronary arteries. The software is discussed further hereinbelow.

Figure 6:
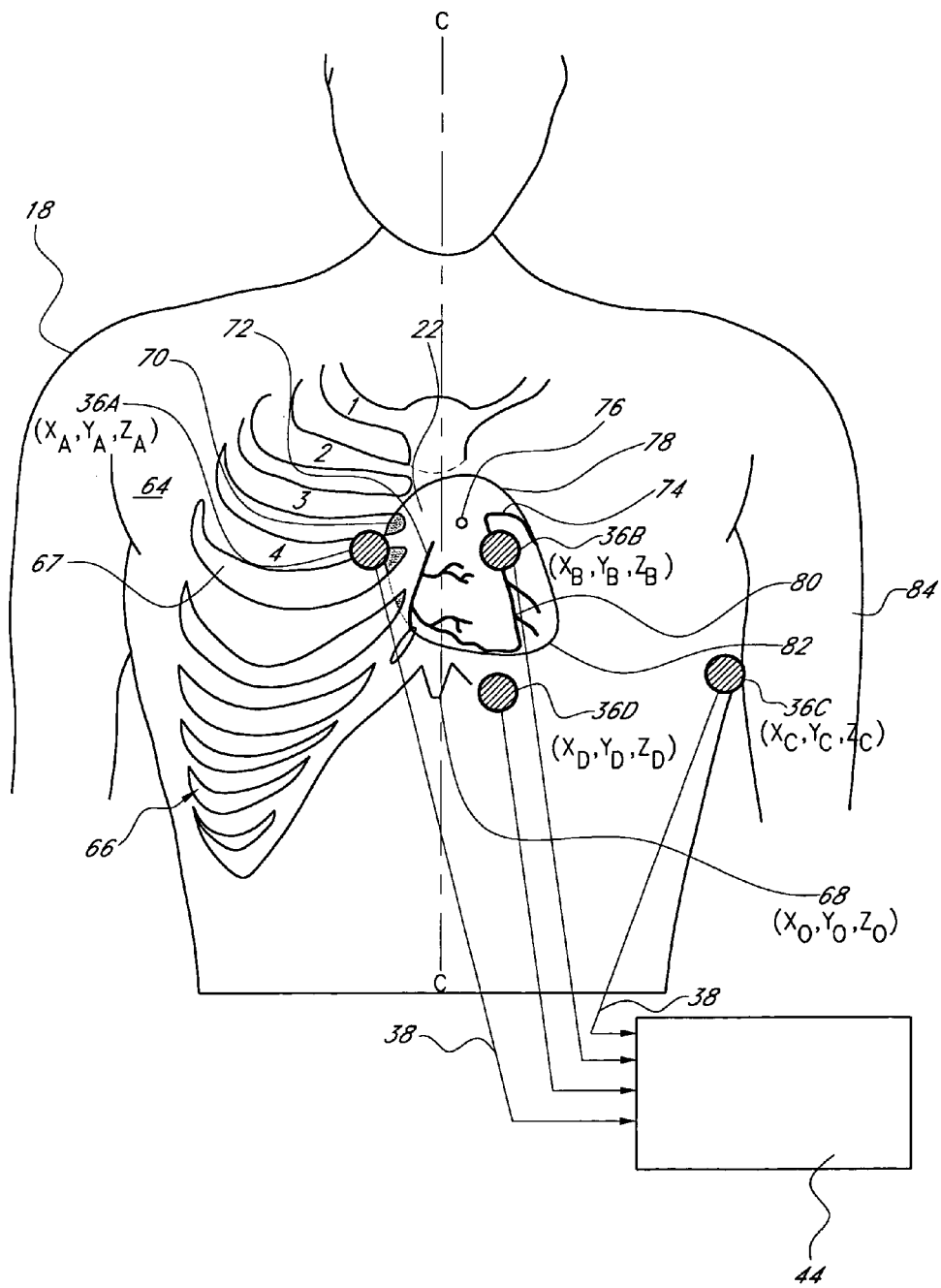
FIG. 6 is an illustration of a plurality of acoustic sensors attached to the chest of a patient as used with the present invention diagnostic tool and method.

Referring to FIG. 6, in operation of the diagnostic tool 24, the sensors 36A-36D are attached to the chest 64 of the patient at known locations with respect to the heart 22, ribs 66, the base of the sternum 68 and a center line C-C. In the illustrated embodiment, the base of the sternum 68 is used as a reference point R having the coordinates $(x_0, y_0, z_0)$. As shown in FIG. 6, a sensor 36A is positioned at a point A, having coordinates $(x_a, y_a, z_a)$, near a right border 70 of the heart 22. Typically, the point A is located on the right side of the chest 64 just above the fourth rib 67 and approximately one inch (1") to the left of the center line C-C (as shown in FIG. 6). FIG. 6 also shows the right and left coronary arteries 72 and 74 of the heart respectively. A stenosis 76 to be detected by the diagnostic tool 24 is shown at a location S having to be determined coordinates $(x_s, y_s, z_s)$. A left border of the heart 22 is identified with the reference numeral 78.

Typically, the sensor 36B is positioned at a point B having the coordinates $(x_b, y_b, z_b)$ that is aligned opposite the sensor 36A and spaced approximately one inch (1") to the right of the center line C-C (as shown in FIG. 6). As shown, the sensor 36B is positioned near the left anterior descending artery 80.

The sensor 36C is located at a point C having the coordinates $(x_c, y_c, z_c)$ and aligned with the apex 82 of the heart 22 on the left side of the patient 18 between the chest 64 and the upper arm 84.

The sensor 36D is located at a point D having the coordinates $(x_d, y_d, z_d)$. The point D is approximately one inch (1") to the right of the center line C-C and aligned with the base of the sternum 68.

Typically all of the sensors 36A-36D are acoustic sensors, such as, for example, microphones or piezo electric crystals. For calibration purposes, an R-Wave sensor is used as the sensor 36D located at the point D.

Figure 7:
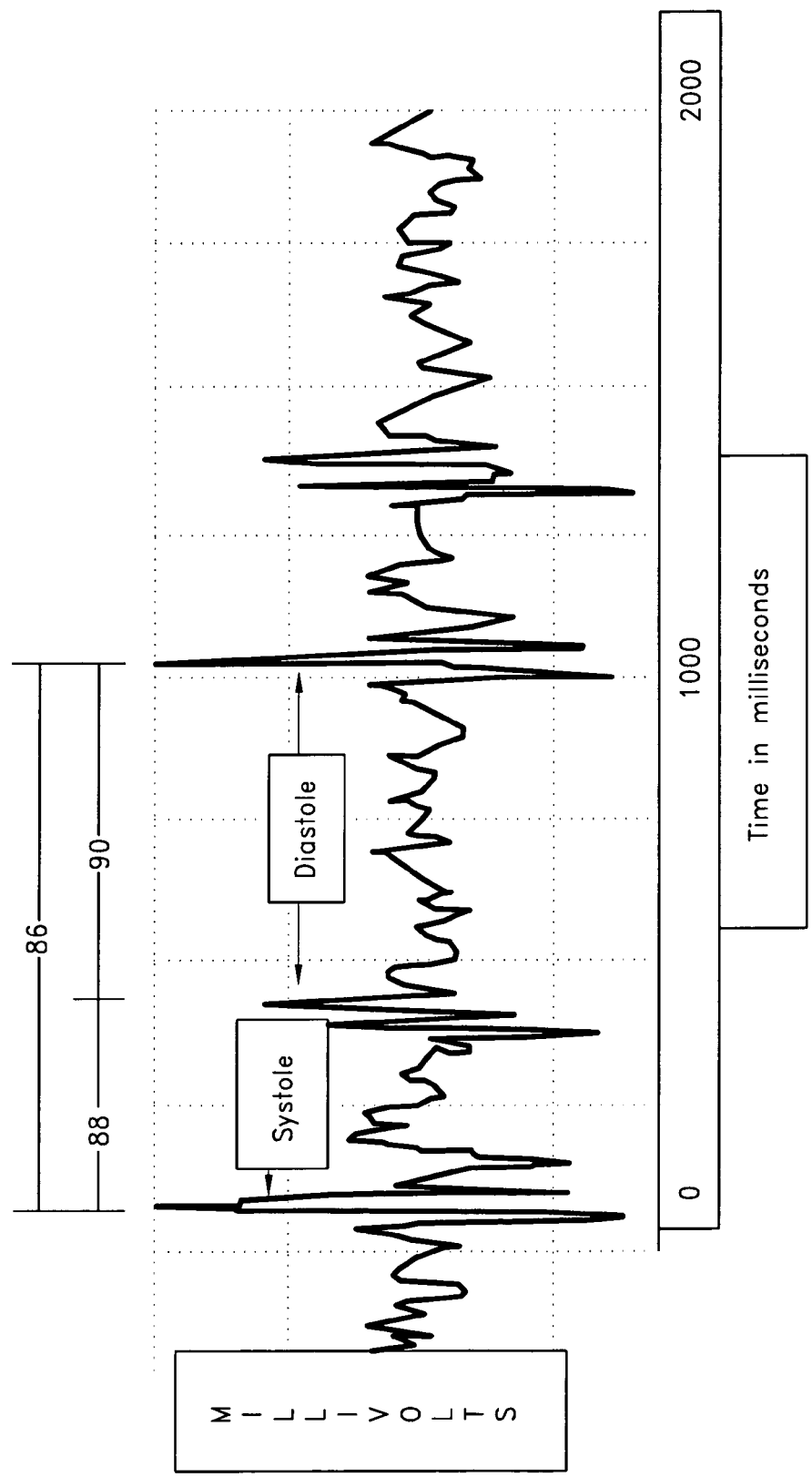
FIG. 7 is a graph of a signal representing a typical heart beat.

FIG. 7 shows a typical heart beat signal wherein the sound of each heartbeat produces a heartbeat signal 86 approximately 1000 milliseconds long. The heartbeat signal 86 includes a systolic signal 88 representing the systolic portion of the heartbeat signal and a diastolic signal 90 representing the diastolic portion of the heartbeat signal. The present invention diagnostic tool 24 utilizes the diastolic signal 90 for identifying a stenosis 76 in the coronary arteries of a patient 18 as well as determining the location $(x_s, y_s, z_s)$ of the stenosis and the Coronary Artery Diagnostic Hurst Occlusion Coefficient (CADHOC) number representing an estimation of the degree of blockage in the artery caused by the stenosis.

Figure 8A:
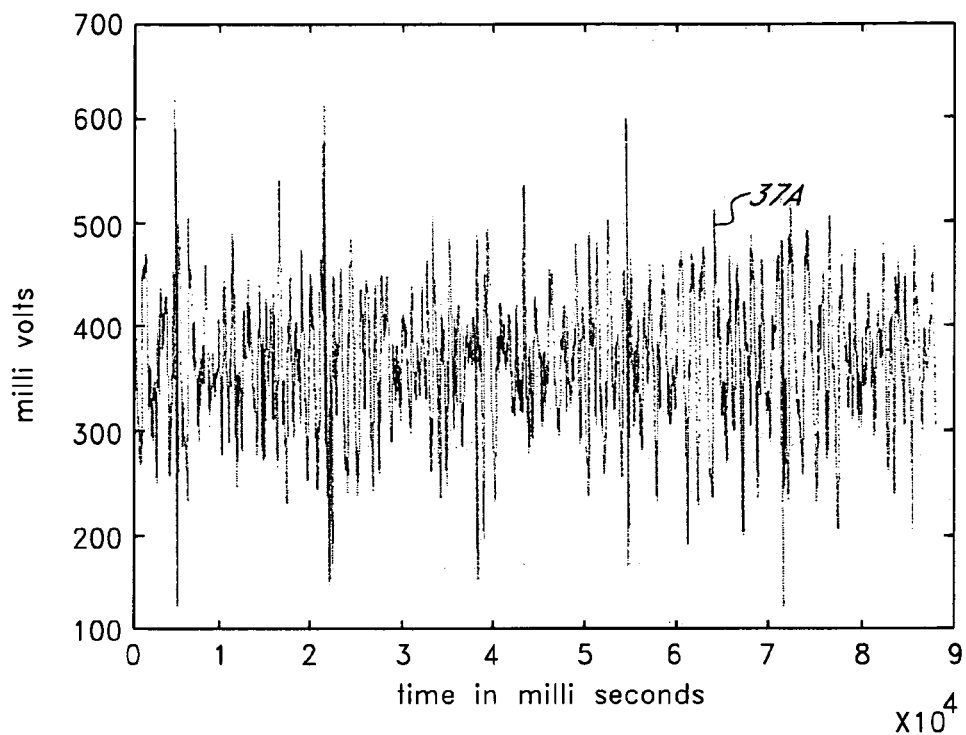
FIGS. 8A-8D are graphs representing the signals received from the sensors of FIG. 6.
Figure 8B:
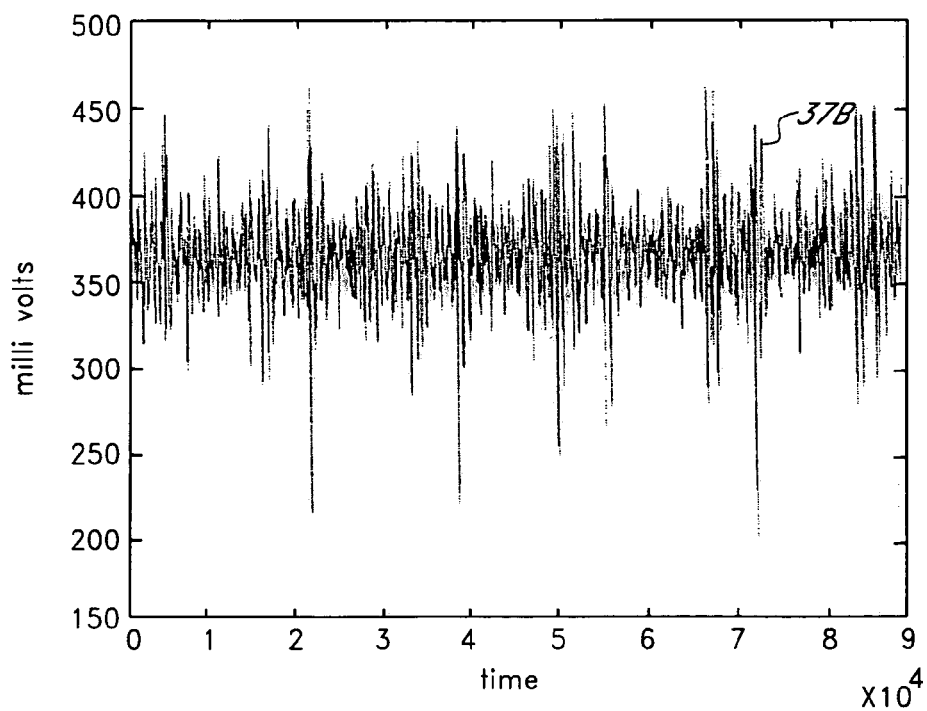
Figure 8C:
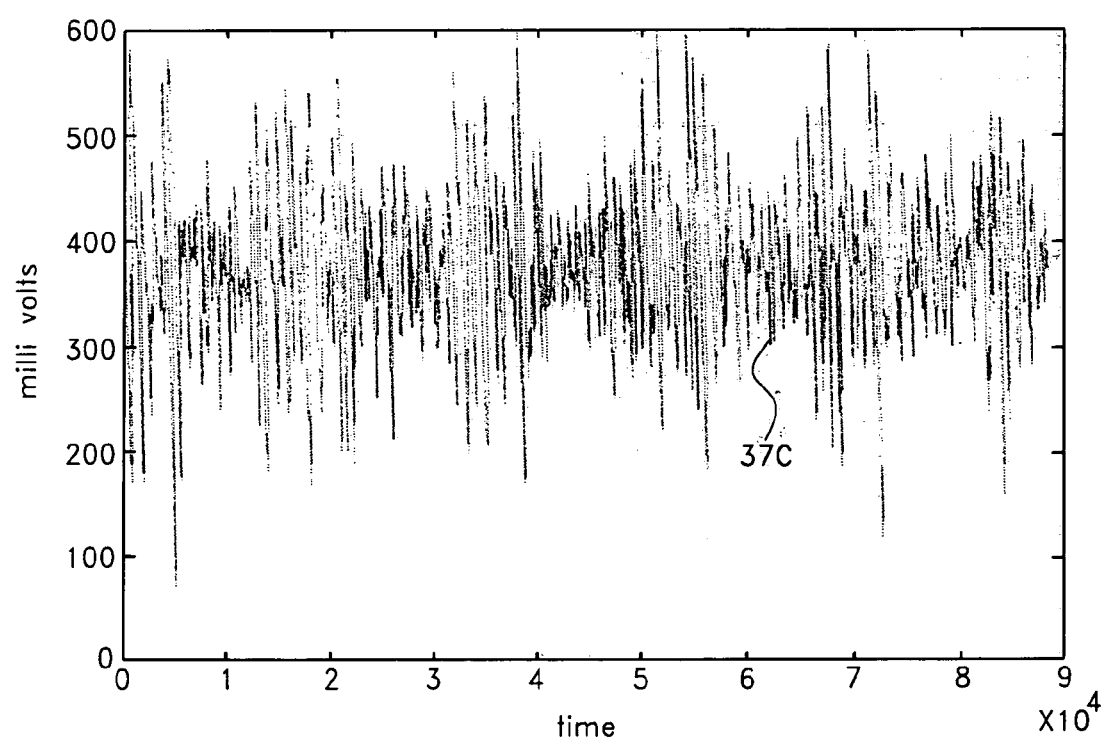
Figure 8D:
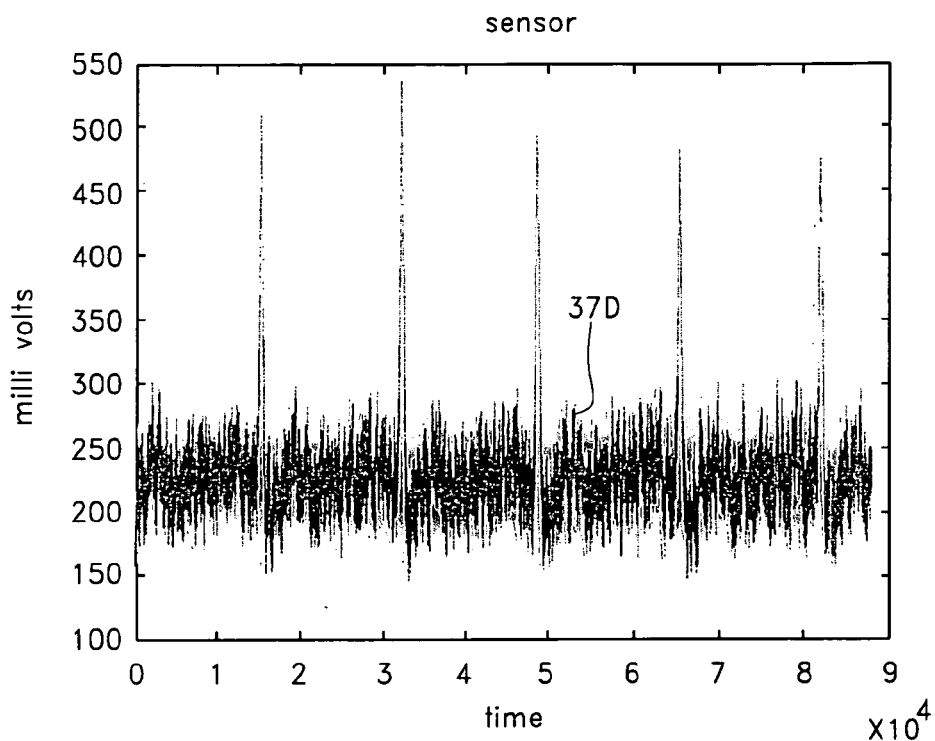
Figure 8E:
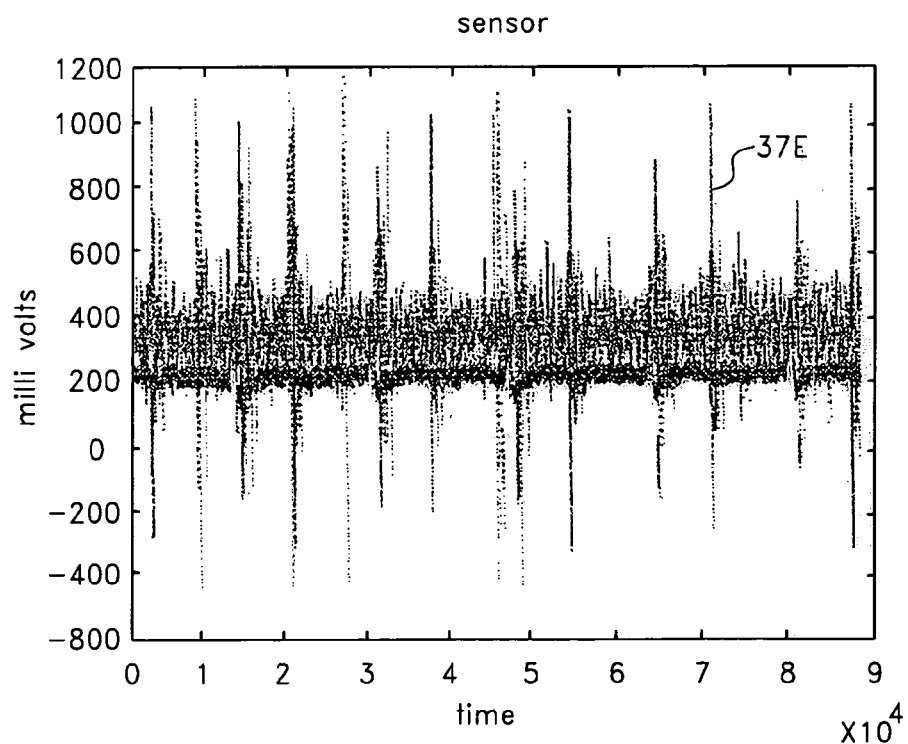
FIG. 8E is a graph showing the signals from the sensor 36D of FIG. 6 superimposed on the signals from a sensor of FIG. 6.

The method of the present invention includes processing the signals received from the sensors 36A-36D using a wavelet transform analysis on the multiplexed signals from the sensors 36A-36D. FIGS. 8A-8D represent samples of the signals 37A-37D received from the sensors 36A-36D respectively. The signals 37A-37D are first analyzed to determine the existence of a triggering pulse vibration that exceeds a predetermined threshold amplitude within a predetermined frequency range. A pulse vibration that exceeds the threshold amplitude indicates the existence of an occlusion in one of the coronary arteries. FIG. 8E represents a signal 37E comprised of the signal 37D superimposed on the signals 37A-37C.

Figure 9:
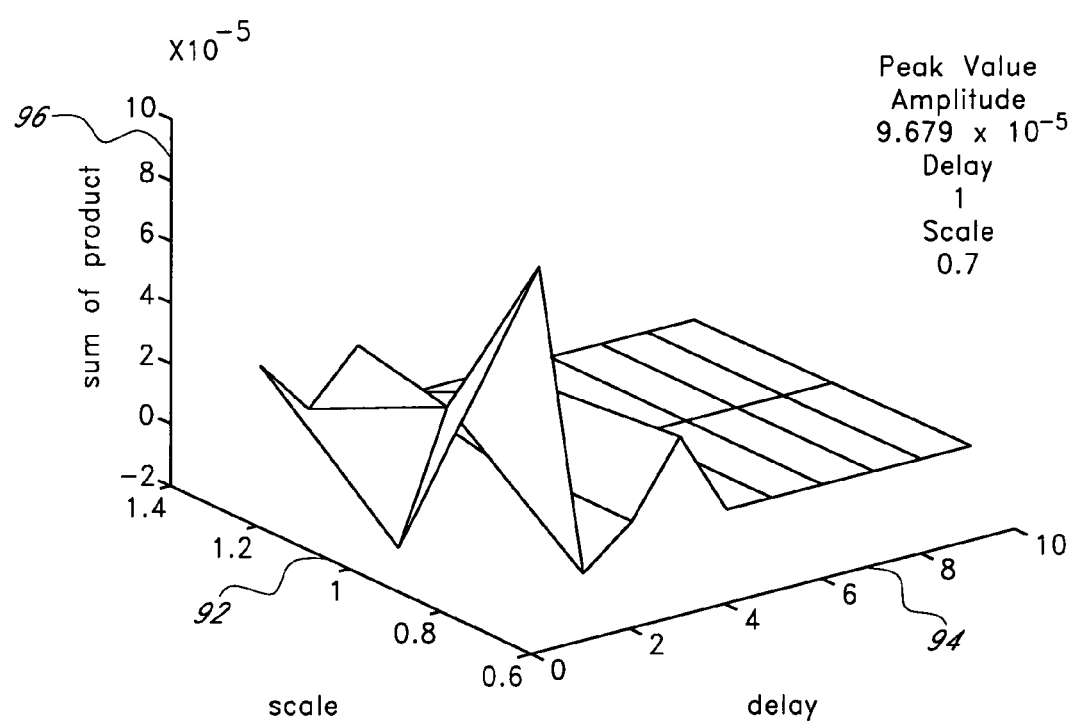
FIG. 9 is an exemplary graph showing a wavelet transform of the signals received from sensors of FIG. 6.

The wavelet transform analysis is conducted on any two of the signals 37A-37D received from the sensors 36A-36D and provides both a frequency and time delay analysis for the signals being analyzed. The wavelet transform is used to calculate the translational delay parameters and the scale parameters between any two of the signals 37A-37D detected by the sensors 36A-36D respectively. FIG. 9 illustrates the evaluation of the wavelet transform coefficients for the scale and translation parameters for the signals received from any two of the sensors 36A-36D. The scaling factor and translation parameters associated with the frequency of the heart sounds during the diastolic signals 90 are used to estimate the time delays for the triggering pulse heart sounds detected by the sensors 36A-36D. These time estimates from the transformed and scaled signals are then evaluated to determine the position of the obstruction or stenosis 76, which generated the high frequency signals during the diastolic signal 90. As shown in FIG. 9, the two horizontal axes 92 and 94 represent the scale and translation parameters respectively. The vertical axis 96 represents the wavelet coefficients.

Figure 10:
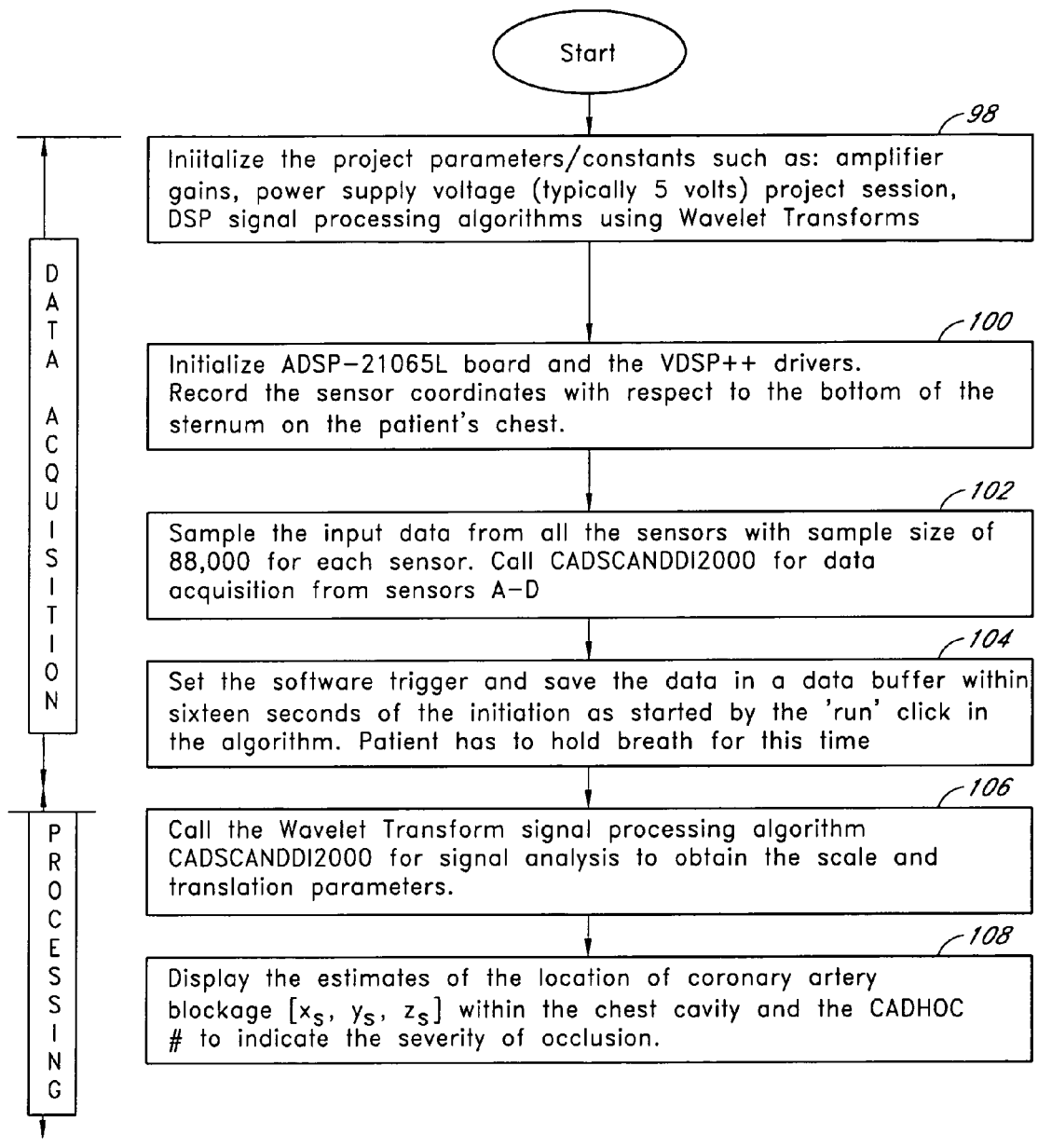
FIG. 10 is a flow chart summarizing the steps of the method of the present invention.

FIG. 10 is a flow chart setting forth the steps of the process of the present invention for determining the location and degree of a stenosis 76 in one of the coronary arteries of the patient 18. At block 98 the components of the processor unit 32 are initialized. At block 100, the coordinates (x, y, z) are recorded for each of the sensors 36A-36D. A sample of the signals 37A-37D generated can be evaluated to ensure the correct operation of the components of the diagnostic tool 24.

At block 102, the signals 37A-37D from each of the sensors 36A-36D are sampled using a sample size of 88,000 for each sensor in the illustrated embodiment. Also a data acquisition routine is called. At block 104, a software trigger is set to identify a triggering pulse having an amplitude in excess of the threshold amplitude and initiates the storage of the data received from the sensors 36A-36D in a data buffer for further processing. In one embodiment of the method of the invention, the patient 18 is directed to hold his/her breath during a predetermined period of time for data acquisition, e.g. 16 seconds.

In a signal processing step (block 104), the multiplexed signals are passed into a data acquisition board, which samples signals in several channels simultaneously at a predetermined minimum sampling frequency per channel, which is determined by the Nyquist Criterion. A clock circuit is employed to time the signals being processed in the multiplexing and processing steps in the DSP core 45.

At block 106, a wavelet transform signal process algorithm is called to process the data acquired from the sensors 36A-36D. The scale and translation parameters are used to determine the location of a stenosis 76. The wavelet coefficients are used to determine the CADHOC number representing the degree of the occlusion.

At block 108, the coordinates of the location of the stenosis ($x_s$, $y_s$, $z_s$) and the CADHOC number representing an estimation of the degree of blockage in the artery caused by the stenosis are shown on the display 28.

Figure 11A:
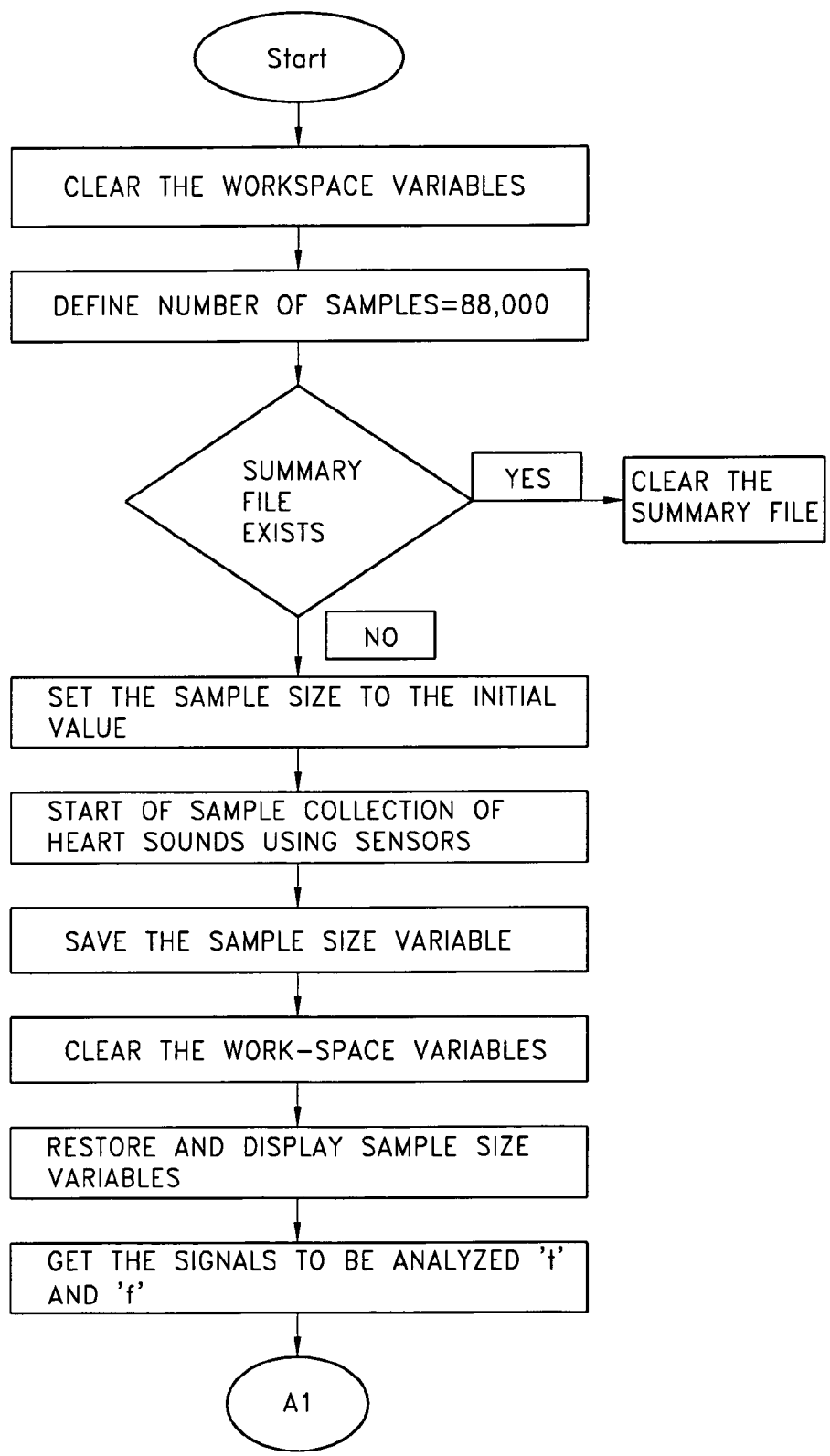
FIGS. 11A-11B illustrate a flow chart showing the steps of the method of the present invention for initializing a diagnostic tool according to the present invention and the acquisition of the signal data from the sensors of FIG. 6.
Figure 11B:
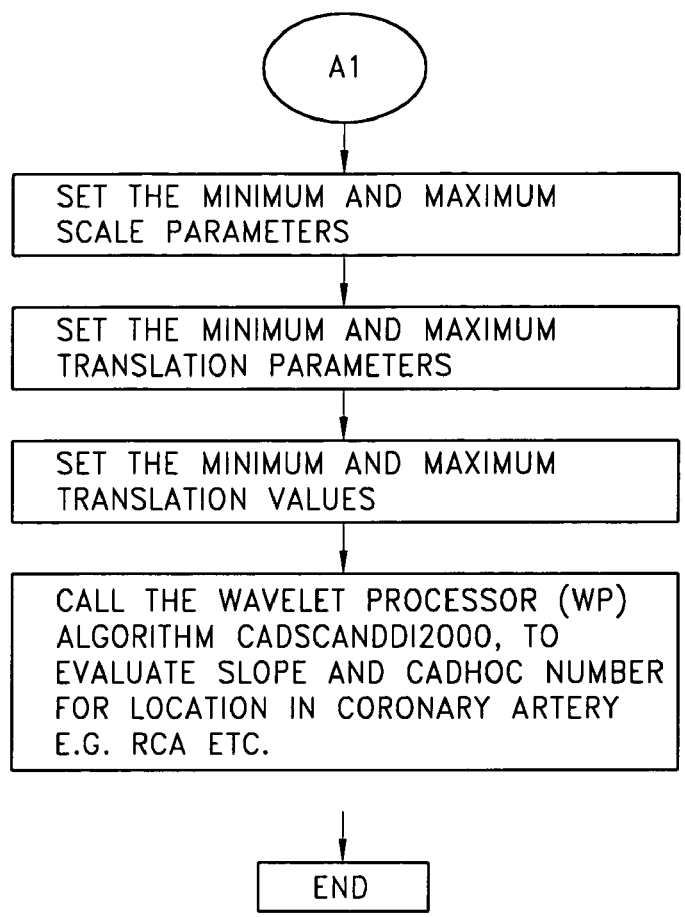
Figure 12A:
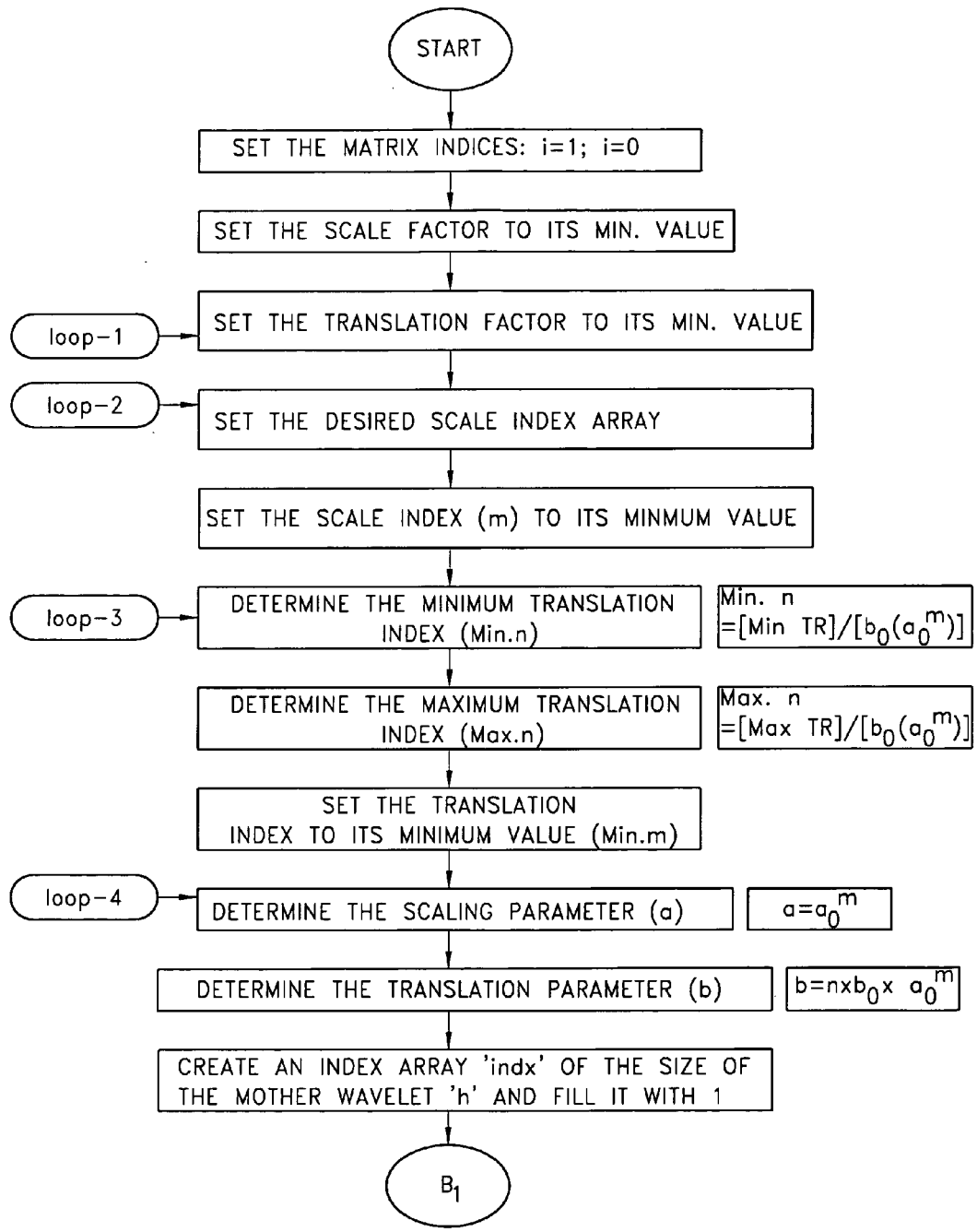
FIGS. 12A-12E illustrate a flow chart setting forth the method steps of the present invention for determining the location and degree of an obstruction in a coronary artery of a patient.
Figure 12B:
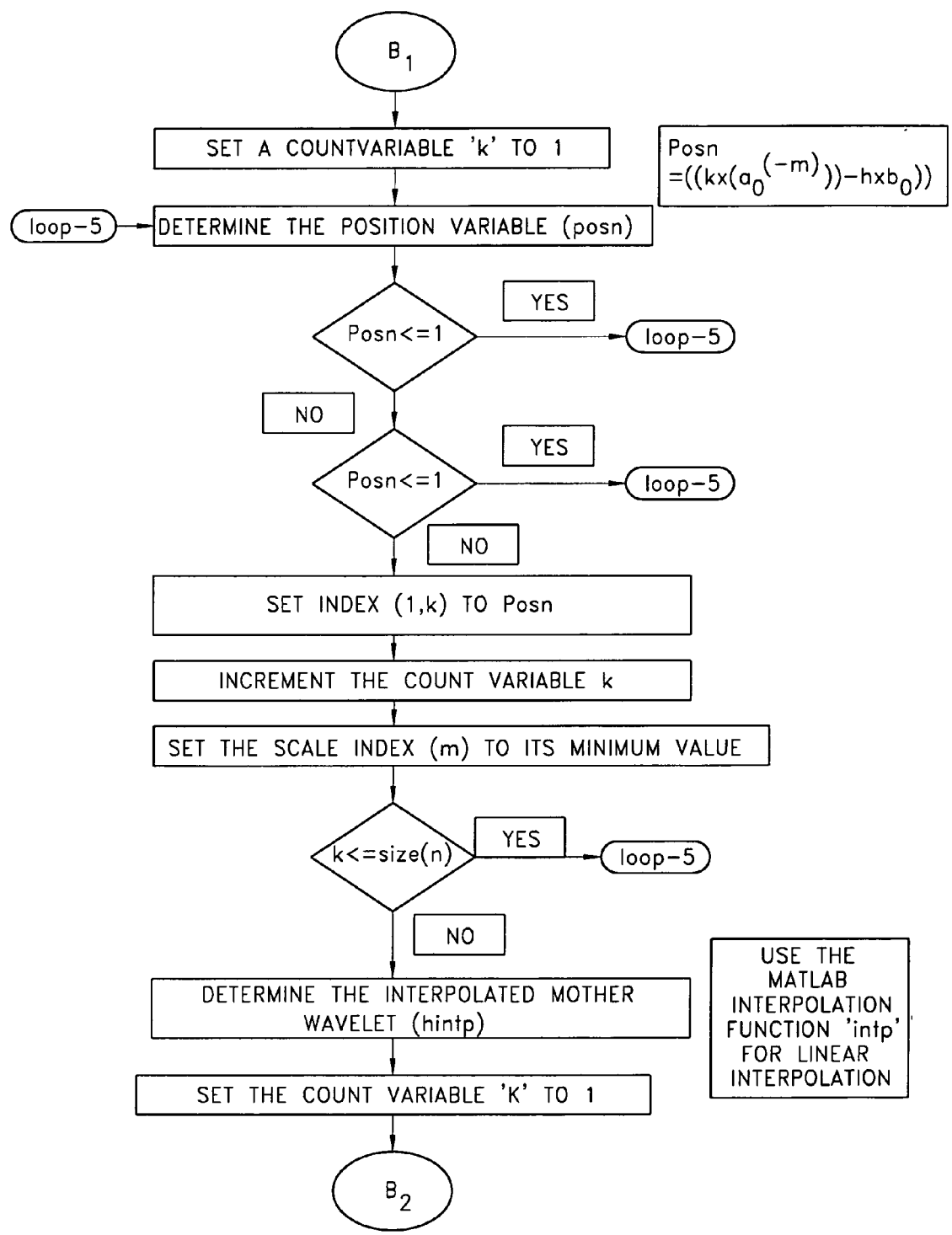
Figure 12C:
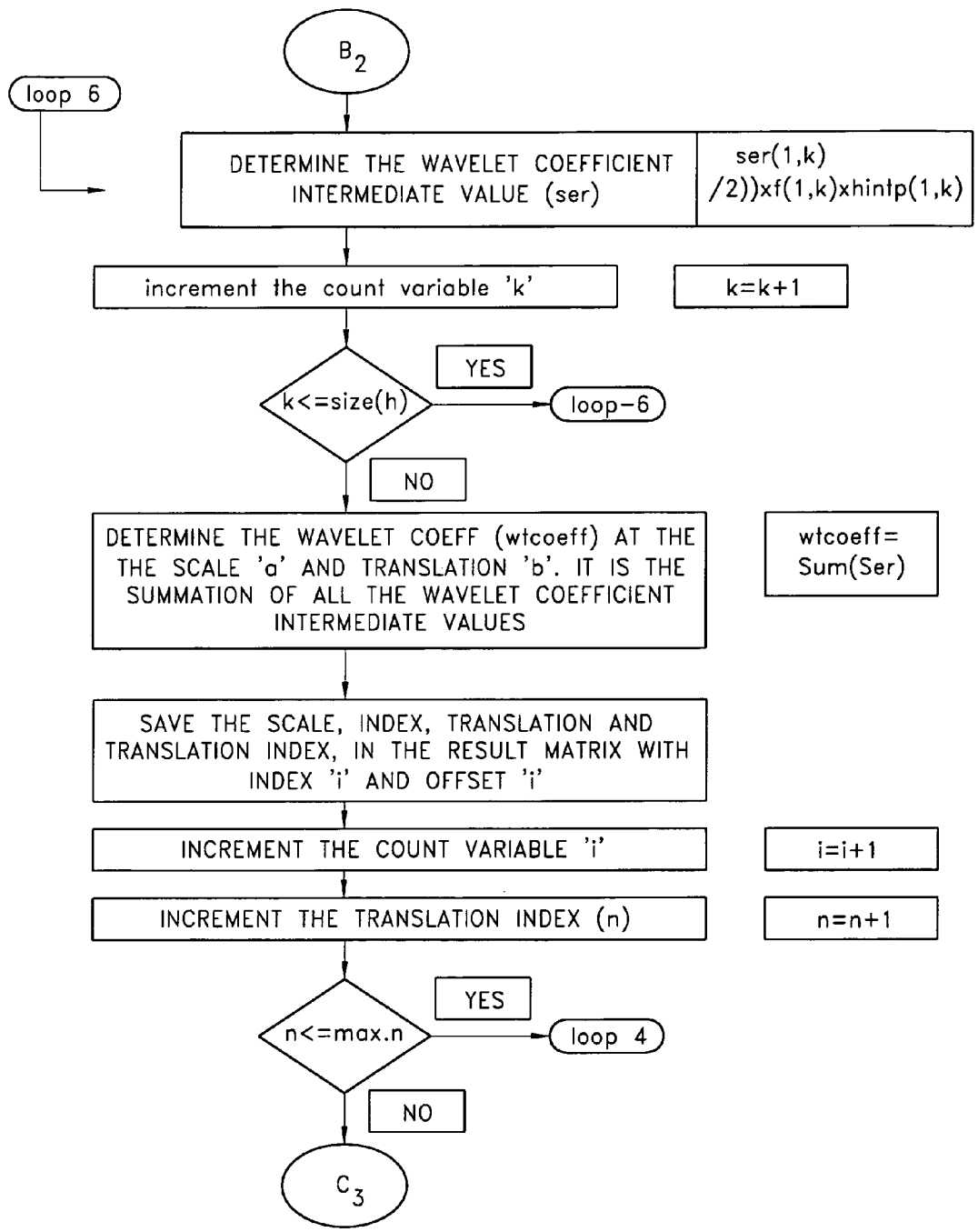
Figure 12D:
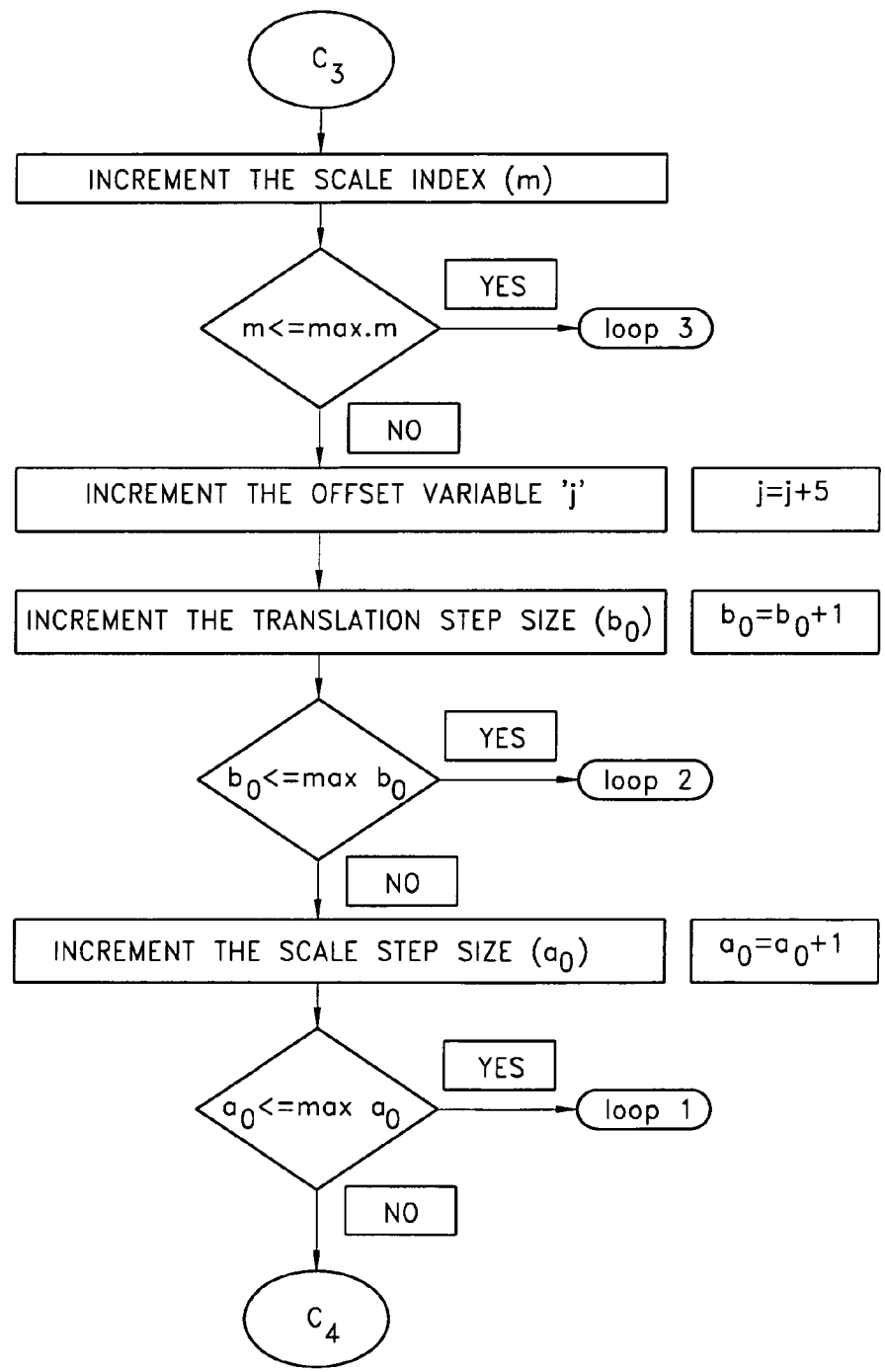
Figure 12E:
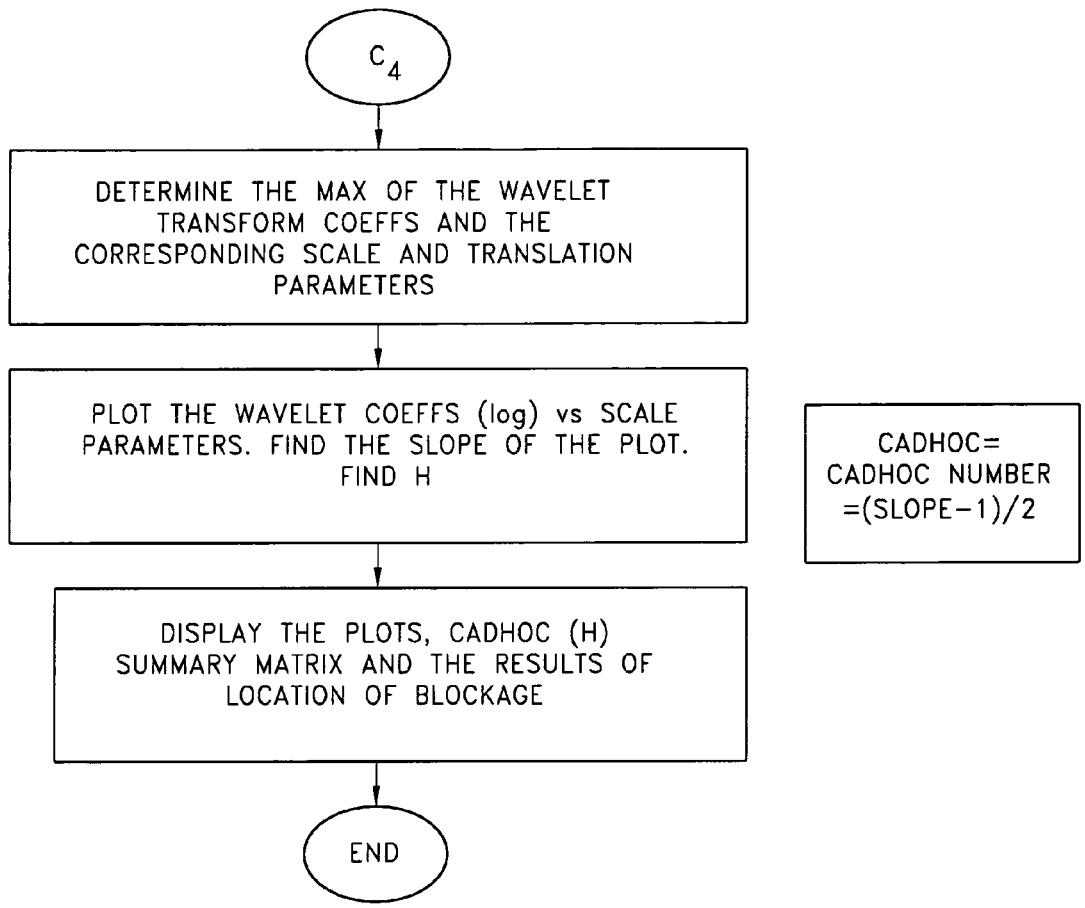

FIGS. 11A and 11B illustrate a flow chart showing the steps of the method of the present invention for initializing the processor unit 44 and the acquisition of the signal data from the sensors 36A-36D. The data collection is started following the initialization of the processor with respect to all of the required parameters, such as amplifier gains, etc. In the illustrated embodiment, the sample size is fixed at 88,000 samples for each sensor 36A-36F that is placed on the chest 64 of the patient 18. The total time needed for the sampling procedure is generally only approximately sixteen seconds. Following or during the data acquisition process, the maximum and minimum values of the scale and the translation parameters are set and saved. The data stored is recalled to be processed by the wavelet transform processor as set forth below.

The coordinates of the location of a possible stenosis 76 occurring at the point ($x_s$, $y_s$, $z_s$) can be identified by calculating the translational delay parameters and the scale parameters by employing a wavelet transform analysis on the signals as shown in FIG. 9. FIG. 9 illustrates the evaluation of the wavelet transform coefficients for the different scale "a" and translation parameters "b" for signals from sensors 36A and 36B. The signals received from any two of the sensors 36A-36F can be evaluated to obtain the location a possible stenosis 76.

All possible combinations of the signals from the sensors 36A-36F are processed using the wavelet transform process, and the corresponding time difference of arrival of the signals are evaluated knowing the speed of sound in the medium inside the chest 64. Since the medium of the patient's chest 64, consists mainly of tissue, bones and blood, a typical value of the speed of sound in blood (water) is chosen as the closest known speed. For example, if the speed of sound in water is "c" feet/sec, then the location of the stenosis 76 is determined by:

$$(x_s - x_i)^2 + (y_s - y_i)^2 + (z_s - z_i)^2 = c^2 \cdot b^2, \quad i = A, B, C, D \quad \quad 1.$$

The location ($x_s$, $y_s$, $z_s$) of the stenosis 76 in the coronary artery is estimated using MATLAB's symbolic logic toolbox and the translation parameter "b" at which the maximum of the wavelet coefficient function occurs.

FIGS. 12A-12E illustrate a flow chart setting forth the method steps for determining the location and degree of the obstruction or stenosis 76. The data received from any two of the sensors 36A-36F are used to compute the wavelet coefficients. The values of the translation and scale parameters where the maximum sum of the wavelet coefficients occurs is saved to determine the optimum value to be used in the location algorithm. This is the value "b" in equation (1) above. The process is completed for all possible combinations of the signals from any two of the sensors 36A-36F. The resulting wavelet coefficients are stored in an array and later utilized to project the variances that are needed to evaluate the CADHOC number as described hereinbelow.

The wavelet coefficients evaluated from the wave transform analysis as set forth above and in the FIGS. 11A-11B and 12A-12E are used to evaluate the CADHOC number as shown below.

The variances of the wavelet coefficients are plotted on a semilog plot for different scale values (a=1 for frequencies 1 KHz to 2 KHz, and a=5 for frequencies of 62.25 Hz to 125 Hz. The CADHOC number is then evaluated by conducting a regression analysis of the log-log plot of estimated variance values of wavelet coefficients versus their scales. The slope of the regression line yields a CADHOC value as follows:

$$CADHOC = (Gama - 1)/2$$

Where, Gama is the slope of the regression line.

The results of the processing from the diagnostic tool 24 are then tabulated as shown in Table 1 following. Table 1 shows the results of the present invention diagnosis tool and method compared with a prior art angiogram report for a patient #1.

TABLE 1

Format of the final CADSCAN results in chart compared to an angiogram result

Patient Name: Patient #1
Description of CAD history: Had no Angioplasty. Came in with chest pain. 2-vessel occlusion.
Final Notes: CADSCAN diagnosis showed a moderate occlusion in the RCA with CADHOC number of 0.34. The entire artery had this blockage. There was no occlusion in the LCA and the LAD, but the LCA revealed severe occlusion in the proximal part with CADHOC number of 0.1.
Eastern CT Cardiologists Association

| | Angiogram | DDI diagnosis with CADSCAN | |
|---|---|---|---|
| | Diagnosis | | CADHOC # |
| RCA | | RCA | 0.34 |
| Proximal | Moderate | Proximal | |
| Middle | | Middle | |
| Distal | Moderate | Distal | |
| Marginal branch | | Marginal Branch | |
| Posterior Ventricular Branch | | Posterior Ventricular Branch | |
| LCA | | LCA | |
| Main | Normal | | |
| Proximal | | | |
| Middle | | | |
| Distal | | | |
| | LAD < 50% | LAD | |
| Proximal | | | |
| Middle | | | |
| Distal | | | |
| 1st diagonal | | | |
| 2nd diagonal | | | |
| | LC | LC | 0.1 |
| Proximal | Moderate | | |
| Middle | | | |
| Distal | | | |

Note:
40-55% Mild Occlusion (CADHOC # = 0.5-0.55)
60-80% Moderate Occlusion (CADHOC # = 0.3-0.49)
>80% Severe Occlusion (CADHOC # = 0.05-0.1)
Legend:
RCA: Right Coronary Artery
LCA: Left Coronary Artery
LAD: Left Anterior Descending
LC: Left Circumflex
CADHOC #—Coronary Artery Diagnostic Hurst Occlusion Component #

The CADHOC number evaluated by the present invention is tabulated in

TABLE 2

| | CADHOC # | |
|---|---|---|
| Description | CADHOC # | Angiogram Occlusion % |
| Mild Occlusion | 0.5-0.55 | 40-55% |
| Moderate Occlusion | 0.3-049 | 60-80% |
| Severe Occlusion | 0.05-0.10 | >80% |

The present invention diagnostic tool 24 and method of use thereof, utilize passive and non-invasive acoustic sensors that provide real time and continuous measurement of heart sounds through the heart 22 and surrounding blood vessels and tissues. The sensors further provide data sample sets that are utilized by signal processing techniques using Wavelet Transforms in accordance with the present invention as set forth above. The signal processing results in the detection of and the location of an obstruction in the coronary arteries of the patient. A real time user interface displays the results of the process for real time monitoring of coronary artery conditions from the collected data signals. Additionally, the present invention provides passive and non-invasive real time monitoring and diagnosis of coronary artery disease in a patient with a portable hand-held device that analyzes and ascertains conditions of the coronary arteries without a surgical procedure.

The foregoing description of embodiments of the present invention diagnosis tool and method have been presented for the purpose of illustration and description and are not intended to be exhaustive or to limit the invention to the form disclosed. Obvious modifications and variations are possible in light of the above disclosure. The embodiments described were chosen to best illustrate the principles of the invention and practical applications thereof to enable one of ordinary skill in the art to utilize the invention in various embodiments and with various modifications as suited to the particular use contemplated. It is intended that the scope of the invention be defined by the claims appended hereto.

What is claimed is:

1. A diagnostic tool for detecting an obstruction in a coronary artery, the diagnostic tool comprising:
   a plurality of passive, non-invasive acoustic sensors and an electrical sensor;
   a data storage unit adapted to store information relating to locations of the acoustic sensors with respect to at least one anatomical feature of a patient; and
   a signal processor adapted to receive and process signals corresponding to a heart beat when the plurality of acoustic sensors and the electrical sensor are attached to the chest of the patient, the signal processor further adapted to receive and process the information relating to locations of the acoustic sensors on the chest of the patient;
   the signal processor being programmed to conduct a wavelet transform on the signals, the wavelet transform providing at least one of a frequency analysis and a time domain analysis for the signals, and
   the signal processor being programmed to identify a diastolic portion of the signals for a plurality of heartbeats, to process information relating to the wavelet transform of the signals, and to determine the severity and the location of an obstruction in a coronary artery, wherein the location of the obstruction is determined at least in part from information relating to the wavelet transform of the signals and the stored information relating to locations of the acoustic sensors.

2. The diagnostic tool according to claim 1 further comprising a display coupled to the signal processor for displaying data indicative of the results of the determination.

3. The diagnostic tool according to claim 1, wherein the signal processor is programmed to determine the severity and the location of the obstruction in the coronary artery based at least in part on the location of at least one of the acoustic sensors and a signal from the electrical sensor.

4. The diagnostic tool according to claim 1 further comprising a user interface coupled to the signal processor.

5. The diagnostic tool according to claim 1 further comprising at least one analog to digital converter coupled to the signal processor and adapted to receive signals from the plurality of acoustic sensors and process the signals including at least one of digitizing, synchronizing and multiplexing the signals, and transmitting the processed signals to the signal processor.

6. The diagnostic tool according to claim 5 further comprising at least one amplifier coupled to the analog to digital converter and adapted to receive the signals from the acoustic sensors and amplify the signals and transmit the amplified signals to the analog to digital converter.

7. The diagnostic tool according to claim 1 wherein the signal processor is a digital signal processor.

8. The diagnostic tool according to claim 1 further comprising an external bus coupled to the signal processor for coupling an external device to the signal processor.

9. The diagnostic tool according to claim 1 further comprising non-volatile memory for initialization of the signal processor.

10. The diagnostic tool according to claim 1 wherein the diagnostic tool is portable.

11. The diagnostic tool according to claim 2, wherein the display is configured to indicate information relating to the presence or the severity of the obstruction.

12. The diagnostic tool according to claim 1, wherein the electrical sensor is an R-wave sensor.

13. The diagnostic tool according to claim 1, wherein the wavelet transform comprises wavelet coefficients and the signal processor is programmed to calculate from the wavelet coefficients a diagnostic number that is indicative of a presence or a severity of an obstruction in the coronary artery.

14. The diagnostic tool according to claim 13, wherein the signal processor is programmed to calculate the diagnostic number from a variance of the wavelet coefficients with respect to a frequency scale parameter.

15. The diagnostic tool according to claim 14, wherein the diagnostic number is determined from the slope of the variance of the wavelet coefficients with respect to the frequency scale parameter.

16. The diagnostic device according to claim 1, wherein the at least one anatomical feature comprises the base of the patient's sternum.

17. The diagnostic device according to claim 1, wherein the at least one anatomical feature comprises a centerline of the patient's chest.

18. The diagnostic device according to claim 1, wherein the at least one anatomical feature comprises a rib of the patient.

19. The diagnostic device according to claim 1, wherein the at least one anatomical feature comprises the patient's heart.

20. The diagnostic device according to claim 1, wherein the data storage unit comprises random access memory.

21. The diagnostic device according to claim 1, wherein the data storage unit comprises nonvolatile memory.

22. The diagnostic device according to claim 21, wherein the nonvolatile memory comprises a flash memory card.

23. The diagnostic device according to claim 1, wherein the information relating to locations of the acoustic sensors comprises locations of the acoustic sensors with respect to a coordinate system.

24. The diagnostic device according to claim 23, wherein the coordinate system comprises a Cartesian coordinate system.

25. The diagnostic device according to claim 1, wherein the information relating to the wavelet transform comprises translational delay parameters of the signals.

26. The diagnostic device according to claim 25, wherein the translational delay parameters are estimated from maxima of a wavelet coefficient function determined from the wavelet transform.

27. The diagnostic device according to claim 1, wherein the location of the obstruction is determined at least in part from information relating to a speed of sound of a medium in the chest of the patient.

28. The diagnostic device according to claim 27, wherein the medium comprises tissue, bones, and blood.

29. The diagnostic device according to claim 27, wherein the medium comprises blood.

30. The diagnostic device according to claim 27, wherein the medium comprises water.

31. The diagnostic device according to claim 1, wherein the location of the obstruction is determined with respect to a coordinate system.

32. The diagnostic device according to claim 31, wherein the coordinate system comprises a Cartesian coordinate system.

* * * * *